US005644033A

United States Patent [19]
Seon

[11] Patent Number: 5,644,033
[45] Date of Patent: Jul. 1, 1997

[54] MONOCLONAL ANTIBODIES THAT DEFINE A UNIQUE ANTIGEN OF HUMAN B CELL ANTIGEN RECEPTOR COMPLEX AND METHODS OF USING SAME FOR DIAGNOSIS AND TREATMENT

[75] Inventor: Ben K. Seon, Williamsville, N.Y.

[73] Assignee: Health Research, Inc., Buffalo, N.Y.

[21] Appl. No.: 994,946

[22] Filed: Dec. 22, 1992

[51] Int. Cl.$^6$ .................................................. C07K 16/28
[52] U.S. Cl. ........................... 530/388.22; 530/388.73; 530/388.85; 435/172.2; 435/334; 435/343.1; 435/344.1; 436/548
[58] Field of Search .................... 530/388.22, 388.73, 530/388.85; 435/240.27, 170.21, 172.2, 810; 436/548

[56] References Cited

FOREIGN PATENT DOCUMENTS

WO92/07574  5/1992  WIPO.

OTHER PUBLICATIONS

Venkitaraman et al., Nature, vol. 352, pp. 777–781 (Aug. 1991).
Seaver, Genetic Engineering News, pp. 10 and 21, (1994).
Köhler et al., Nature, vol. 256, pp. 495–497 (1975).
Köhler et al., Eur. J. Immunol. vol. 6, pp. 511–519 (1976).
Gaifre et al., Methods in Enzymology, vol. 73, pp. 3–47, (1975).
Goding, Journal of Immunological Methods, vol. 39, pp. 285–308 (1980).
Galton et al. "Prolymphocytic leukemia", British J. Haematol, 27: 7, 1974.
Catovsky "Prolymphocytic and hairy cell leukemias", in Henderson ES, Lister TA (eds): Leukemia, Philadelphia, PA, Saunders, 1990, p. 639.
Bearman et al. "Prolymphocytic leukemia: Clinical, histopathological, and cytochemical observations", Cancer 42: 2360, 1978.
Katayama et al. "B–lineage prolymphocytic leukemia as a distinct clinicopathologic entity", Am. J. Pathol. 99: 399, 1980.
Melo et al. "The relationship between chronic lymphocytic leukaemia and prolymphocytic leukaemia: I. Clinical and laboratory features of 300 patients and characterization of an intermediate group", British J. Haematol, 63: 377, 1986.
Foon et al. "Immunologic classification of leukemia and lymphoma", Blood, 68: 1, 1986.
Han et al. "Chronic lymphocytic leukemia", in Henderson ES, Lister TA (eds): Leukemia, Philadelphia, PA, Saunders, 1990, p. 565.
Seon et al. "Monoclonal antibody that defines a unique human T–cell leukemia antigen", Proc. Natl. Acad. Sci. USA, 80: 845, 1983.
Takeuchi et al. "Monoclonal antibody SN10 which shows a highly selective reactivity with human B leukemia–lymphoma and is effectively internalized into cells", Cancer Res., 51:2985, 1991.
Haruta et al. "Distinct human leukemia–associated cell surface glycoprotein GP160 defined by monoclonal antibody SN6", Proc. Natl. Acad. Sci., USA, 83: 7898, 1986.
Fukukawa et al. "New monoclonal antibodies SN3, SN3a and SN3b directed to sialic acid of glycoprotein on human non–T leukemia cells" Exp Hematol 14: 850, 1986.
Luo et al. "Establishment of ascitic tumor of human pre–B acute lymphoblastic leukemia in nonconditioned nude mice", Cancer Res., 49: 706, 1989.
Matsuzaki et al. "Unique epitopes of common acute lymphoblastic leukemia antigen detected by new monoclonal antibodies", Cancer Res., 47: 2160, 1987.
Seon et al. "Human T cell leukemia antigens on the cell membranes: Purification, molecular characterization, and preparation of specific antisera", J. Immunol, 127: 2580, 1981.
Negoro et al. "Strong, specific anti–human leukemia antisera prepared with the use of purified cell membrane antigen", Cancer Res., 41: 2973, 1981.
Seon et al. "Monoclonal antibody SN2 defining a human T–cell leukemia–associated cell surface glycoprotein", J. Immunol., 132: 2089, 1984.
Sunaga et al. "Detection of sulfur–containing compounds in control and cadmium–exposed rat organs by high–performance liquid chromatography–vacuum–ultraviolet inductively coupled plasma–atomic emission spectrometry (HPLC–ICP)", Anal. Biochem., 160: 160, 1987.
Matsuzaki et al. "Molecular nature of a cell membrane antigen specific for human T–cell acute lymphoblastic leukemia", Cancer Res., 47: 4283, 1987.
Inman et al. "Characterization of Sequential immune complexes in infective endocarditis by Western blot analysis", J. Immunol, 133: 217, 1984.
Trucco et al. "Quantitative analysis of cell surface HLA structures by means of monoclonal antibodies", Human Immunol., 3: 233, 1980.

(List continued on next page.)

Primary Examiner—Toni R. Scheiner
Attorney, Agent, or Firm—Michael L. Dunn

[57] ABSTRACT

Three monoclonal antibodies defining extracellular epitopes of a unique heterodimeric glycoprotein complex consisting of the human mb-1 protein and the human B29 protein which react with one or more leukemia lymphoma cell specimens selected from the group consisting of B prolymphocytic leukemia cells, B non-Hodgkin's lymphoma cells, B chronic lymphocytic leukemia cells, B hairy cell leukemia cells, and B acute lymphoblastic leukemia cells. The three monoclonal antibodies also react with human non-malignant B cells. The invention also provides a method for producing the new monoclonal antibodies and for diagnostic procedures using the monoclonal antibodies and for the treatment of leukemia-lymphoma patients and patients with immunological diseases. The invention also relates to the isolation and chemical identification of the human B29 and mb-1 proteins of B cell antigen receptor complex. The amino-terminal amino acid sequences of the mb-1 and B29 gene products were determined.

12 Claims, 12 Drawing Sheets

OTHER PUBLICATIONS

Seon et al. "Human T-cell leukemia-associated cell surface glycoprotein GP37: Studies with three monoclonal antibodies and a rabbit antiserum", *Mol. Immunol.,* 23: 569, 1986.

Luo et al. "Marked difference in the in vivo antitumor efficacy between two immunotoxins targeted to different epitopes of common acute lymphoblastic leukemia antigen (CD10): Mechanisms involved in the differential activities of immunotoxins", *J. Immunol.,* 145: 1974, 1990.

Hara et al. "Efficient transplantation of human non-T-leukemia cells into nude mice and induction of complete regression of the transplanted distinct tumors by ricin A-chain conjugates of monoclonal antibodies SN5 and SN6", *Cancer Res.,* 48: 4673, 1988.

Knowles et al. "Purification of immunotoxins containing ricin A-chain and abrin A-chain using Blue Sepharose CL-6B", *Anal. Biochem.,* 160: 440, 1987.

Boyse et al. "Antigenic properties of experimental leukemias. II. Immunological studies in vivo with C57BL/6 radiation-induced leukemias" *J. Natl. Cancer Inst.,* 31: 987, 1963.

Ritz et al. "Modulation of human acute lymphoblastic leukemia antigen induced by monoclonal antibody in vitro" *J. Immunol.,* 125: 1506, 1980.

Zola, "The surface antigens of human B lymphocytes", *Immunol. Today,* 8: 308, 1987.

Magrath et al. "Bone marrow involvement in Burkitt's lymphoma and its relationship to acute B-cell leukemia" *Leukemia Res.,* 4: 33, 1979.

LeBien et al. "Use of monoclonal antibodies, morphology, and cytochemistry to probe the cellular heterogeneity of acute leukemia and lymphoma" *Cancer Res.,* 41: 4776, 1981.

Jaffe "The role of immunophenotypic markers in the classification of non-Hodgkin's lymphomas" *Seminars Oncol.,* 17: 11, 1990.

Luzzatto et al. "DNA rearrangements of cell lineage specific genes in lymphoproliferative disorders" *Prog. Hematol.,* 14: 303, 1986.

Vitetta et al. "Redesigning nature's poison to create anti-tumor reagents" *Science,* 238: 1098, 1987.

Vallera et al. "Immunoconjugates" in Chiao JW (ed), *Biological Response Modifiers and Cancer Research,* New York, Dekker, 1988, p. 17.

Seon et al. "Anti-human leukemia monoclonal antibodies and immunotoxins for complete growth suppression of tumor cells in vitro and in vivo", in Torisu M, Yoshida T (eds); *New Horizons of Tumor Immunotherapy,* Amsterdam, Elsevier Science Publishers, 1989, p. 329.

Gold et al. "Stimulation of protein tyrosine phosphorylation by the B-lymphocyte antigen receptor", *Nature,* 345: 810, 1990.

Campbell et al. "Protein tyrosine phosphorylation is induced in murine B lymphocytes in response to stimulation with anti-immunoglobulin", *EMBO J.,* 9: 2125, 1990.

Clark et al. "Regulation of human B-cell activation and adhesion" *Annu. Rev. Immunol.,* 9: 97, 1991.

Cambier et al. "Membrane immunoglobulin and its accomplices: new lessons from an old receptor" *FASEB J.,* 6: 3207, 1992.

Reth, "Antigen receptors on B lymphocytes", *Annu. Rev. Immunol.,* 10: 97, 1992.

Pernis et al. "Immunoglobulins as cell receptors" *Ann. N.Y. Acad. Sci.* 190: 420, 1972.

Hombach et al. "A novel 34 kD protein co-isolated with IgM molecule in surface IgM-expressing cells" *EMBO J.* 7: 3451, 1988.

Hombach et al. "Molecular components of the B-cell antigen receptor complex of the IgM class" *Nature,* 343: 760, 1990.

Campbell et al. "B lymphocyte antigen receptors (mIg) are non-covalently associated with a disulfide-linked, inducibly phosphorylated glycoprotein complex", *EMBO J.* 9: 441, 1990.

Sakaguchi et al. "B lymphocyte lineage restricted expression of mb-1, a gene with CD3-like structural properties" *EMBO J.,* 7: 3457, 1988.

Hermanson et al. "A member of the immunoglobulin gene superfamily exclusively expressed on B-lineage cells" *Proc. Natl. Acad. Sci. USA,* 85: 6890, 1988.

Hombach et al. "Identification of the genes encoding the IgM-α and Ig-β components of the IgM antigen receptor complex by amino-terminal sequencing" *Eur. J. Immunol,* 20: 2795, 1990.

Okazaki et al. "Monoclonal antibody directed to prolymphocytic leukemia" *Proc. Am. Assoc. Cancer Res.* (Abstract) 30: 350, 1989.

Okazaki et al. "Three new monoclonal antibodies that define a unique antigen associated with prolymphocytic leukemia/non-Hodgkin's lymphoma and are effectively internalized after binding to the cell surface antigen" *Blood,* 81: 84, 1993.

Takeuchi et al. "Monoclonal antibody SN10 which shows a highly selective reactivity with human B leukemia-lymphoma and is effectively internalized into cells" *Cancer Res.,* 51: 2985, 1991.

Miyoshi et al. "Human B cell, T cell and null cell leukaemic cell lines derived from acute lymphoblastic leukemias" *Nature* 267: 843, 1977.

Seon et al. "Monoclonal antibody that defines a unique human T cell leukemia antigen" *Proc. Natl. Acad. Sci.,* USA 80: 845, 1983.

Haruta et al. "Distinct human leukemia-associated cell surface glycoprotein GP160 defined by monoclonal antibody SN6" *Proc. Natl. Acad. Sci.,* USA, 83: 7898, 1986.

Matsudaira "Sequence from picomole quantities of proteins electroblotted onto polyvinylidene difluoride membranes" *J. Biol. Chem.,* 262: 10035, 1987.

Nakamura et al. "Heterogeneity of immunoglobulin-associated molecules on human B cells identified by monoclonal antibodies" *Proc. Natl. Acad. Sci.,* USA, 89: 8522, 1992.

Clark et al. "Human pre-B and B cell membrane μ-chains are noncovalently associated with a disulfide-linked complex containing a product of the B29 gene" *J. Immunol.* 149: 2857, 1992.

Muller et al. "Cloning and sequencing of the cDNA encoding the human homologue of the murine immunoglobulin-associated protein B29" *Eur. J. Immunol.,* 22: 1621, 1992.

Yu et al. "Human mb-1 gene: Complete cDNA sequence and its expression in B cells bearing membrane Ig of various isotypes" *J. Immunol.,* 148: 633, 1992.

Ha et al. "Molecular cloning and expression pattern of a human gene homologous to the murine mb-1 gene" *J. Immunol.* 148: 1526, 1992.

Campbell et al. "α-Chains of IgM and IgD antigen receptor complexes are differentially N-glycosylated MB-1-related molecules" *J. Immunol.* 147: 1575, 1991.

Van Noesel et al. "Identification of two distinct phosphoproteins as components of the human B cell antigen receptor complex" *Eur. J. Immunol.*, 20: 2789, 1990.

Van Noesel et al. "The membrane IgM–associated heterodimer on human B cells is a newly defined B cell antigen that contains the protein product of the mb–1 gene" *J. Immunol.* 146: 3881, 1991.

Seon et al. "Human T cell leukemia antigens on the cell membranes: Purification, molecular characterization, and preparation of specific antisera" *J. Immunol.* 127: 2580, 1981.

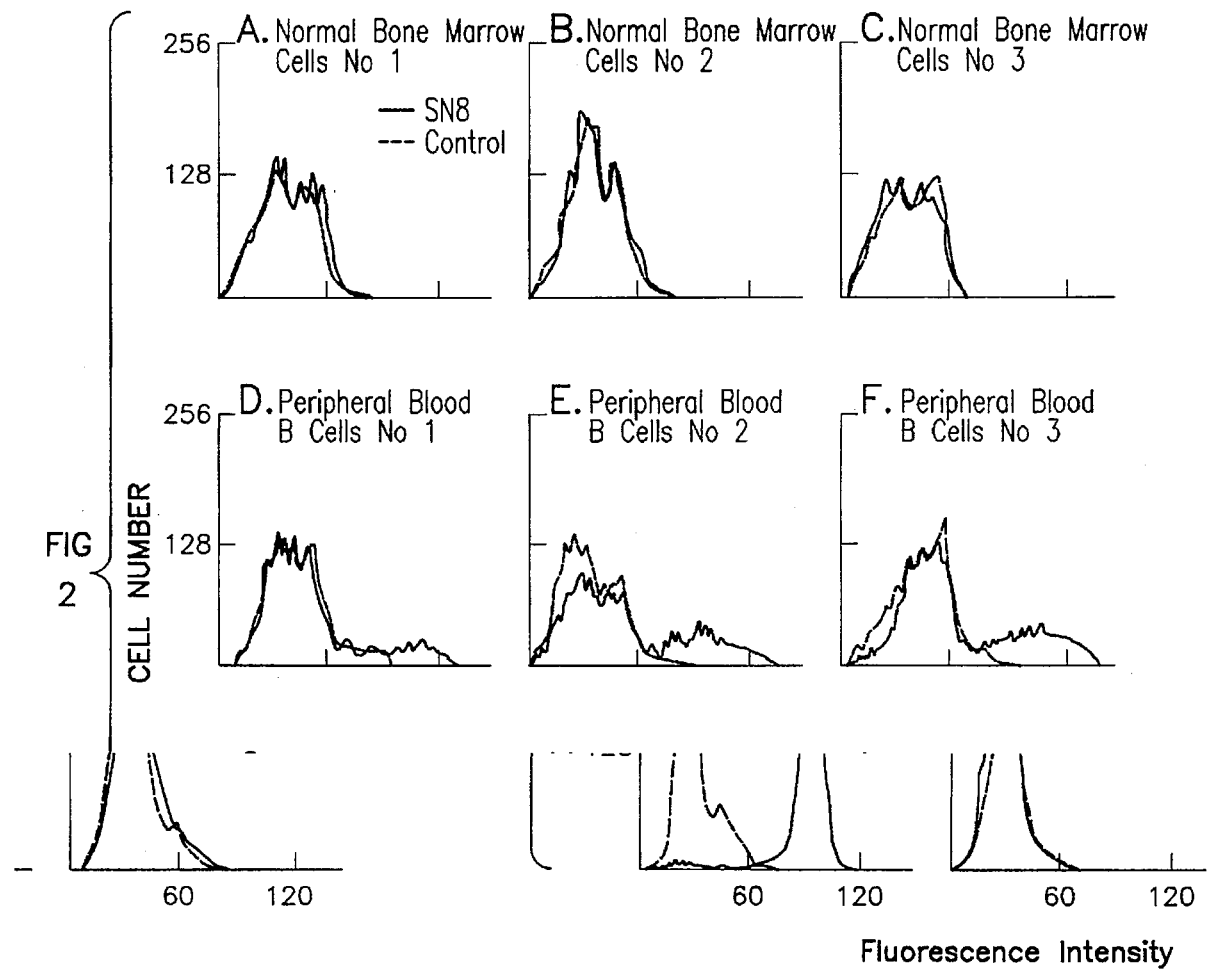

Ala Arg Ser Glu Asp Arg Tyr Arg Asn Pro Lys Gly Ser Ala ND ND Arg
       5              10              15

Leu ND Met His Lys Val Pro Ala Ser Leu Met Val Ser Leu Gly Glu Asp Ala His Phe
     5              10              15              20

FIG 11

MONOCLONAL ANTIBODIES THAT DEFINE A UNIQUE ANTIGEN OF HUMAN B CELL ANTIGEN RECEPTOR COMPLEX AND METHODS OF USING SAME FOR DIAGNOSIS AND TREATMENT

The invention herein was made in the course of work under a grant or award from the American Cancer Society and the National Cancer Institute.

BACKGROUND OF THE INVENTION

This invention relates to three novel monoclonal antibodies (mAbs) termed SN8, SN8a and SN8b which are directed toward individually different epitopes of the same antigen molecule, which is primarily expressed on B-cell type B prolymphocytic leukemia (PLL) cells, B non-Hodgkins' lymphoma (NHL) cells, B acute lymphoblastic leukemia (ALL), and to methods of using the monoclonal antibodies, in whole or in part, for the diagnosis and therapy of various human leukemia-lymphomas (HLL), especially PLL and NHL.

Prolymphocytic leukemia (PLL) was initially reported in 1974 by Galton et al. as a variant of chronic lymphocytic leukemia (CLL), but with distinct clinical and laboratory features ("Prolymphocytic Leukemia", British J. Haematol, 27: 7, 1974). The distinction between PLL and CLL is clinically important because PLL is a relentlessly progressive disease with a worse prognosis and usually resistant to the chemotherapy that is often effective in CLL (Catovsky, "Prolymphocytic and hairy cell leukemias", in Henderson E. S., Lister T. A. (eds): Leukemia, Philadelphia, Pa., Saunders, 1990, p. 639). The majority (approximately 75%) of PLL cases are of B cell origin as are most cases (approximately 98%) of CLL (Foon et al., "Immunologic classification of leukemia and lymphoma", Blood, 68: 1, 1986). Furthermore, B PLL appears to be closely related to hairy cell leukemia (HCL) in the differentiation pathway of B cell ontogeny.

SN8 was capable of effectively distinguishing B PLL from B CLL as well as from hairy cell leukemia (HCL) cell specimens. SN8a and SN8b also showed a selective reactivity with B PLL and B NHL samples. However, these mAbs reacted with higher percentages of CLL samples compared to SN8. Thus, the degree of PLL selectivity of these mAbs is less than that of SN8.

Recent study of the chemical structure of the SN8 antigen revealed that SN8 antigen is a novel heterodimer antigen which constitutes the human B cell antigen receptor complex together with cell membrane immunoglobulin.

Antigen receptors on B lymphocytes (B cells) play a central role in the immune regulation in animals and humans. In the case of the murine B cells, two disulfide-linked transmembrane molecules, encoded by the mb-1 and B29 genes, have been recently defined as integral components of the antigen receptors on murine B cells. The mb-1 and B29 products are termed Ig-$\alpha$ and Ig-$\beta$, respectively. A variant form of the Ig-$\beta$ was called Ig-$\gamma$. The disulfide-linked heterodimer $\alpha$-$\beta$ molecules on B cells are noncovalently associated with cell membrane immunoglobulins (mIgs). Recent studies by several investigators suggest that a similar situation exists for the antigen receptor complex on human B cells. However, the human homologues of murine mb-1 and B29 gene products have not been definitely identified.

The present invention discloses the generation and characterization of three mAbs termed SN8, SN8a and SN8b that were generated by immunizing two mice with an isolated PLL antigen preparation. These mAbs, particularly SN8, showed a highly selective reactivity with B PLL and B NHL. The surface antigen defined by the SN8 series mAbs was identified as a covalently-linked heterodimer (gp49/40). Comparison of SN8 series mAbs and SN8 antigen with the reported mAbs and their antigens suggests that SN8 series mAbs define a novel B-cell antigen.

This conclusion was corroborated by the determination of the amino-terminal amino acid sequences of the individual components ($\alpha$ and $\beta$ chains) of the SN8 antigen. The amino acid sequence study revealed unequivocally that the $\alpha$ (47–49 kD) and $\beta$ chain (37–40 kD) components of the SN8 antigen are the human mb-1 and B29 proteins, respectively. In the amino acid sequence study, the non-radiolabeled SN8 antigen was isolated from human B leukemia cells using SN8 immunoaffinity column. Use of SN8 was indispensible for the isolation and immunological analysis of the human mb-1 and B29 heterodimer in the present study. For unknown reasons, it is extremely difficult to generate a mAb defining the human B29 or mb-1 protein by conventional approach, i.e., immunizing mice with human B cells. Thus, few mAbs specific for an extracellular epitope of the human B29 or mb-1 protein have been previously reported. An exception is a recent report by Nakamura et al. ("Heterogeneity of immunoglobulin-associated molecules on human B cells identified by monoclonal antibodies", Proc. Natl. Acad. Sci. USA, 89: 8522, 1992) who generated two mAbs defining the putative human equivalent of the mouse B29 protein. They used an elaborate procedure including repeated injections of mice with proteins separated by SDS-PAGE. Nakamura et al. used the phrase "putative human equivalent of the mouse B29 protein" because they had neither characterized the antigen chemically nor determined the antigen's amino acid sequence. Also, it appears that no amino acid sequence of the human B29 or mb-1 proteins has been reported prior to the present invention.

Since the present mAbs show a highly selective reactivity as well as high binding avidity (SN8 and SN8b) and are of IgG1 isotype, they may be useful for the diagnosis of B leukemia/lymphoma, for studying the pathogenesis of PLL and perhaps for studying normal human B cell differentiation.

In addition, ricin A-chain (RA) conjugates of the three mAbs are all effective for the specific killing of SN8 antigen-expressing cells. Furthermore, binding of these mAbs to the cell surface antigen induced no significant (SN8 and SN8b) or only a small (SN8a) down-regulation of antigen expression. The results suggest the potential of these mAbs as a specific delivery vehicle of cytotoxic agents to the SN8 antigen-expressing target cells.

The B cell antigen receptor complex plays a central role in the immune regulation in the human. Therefore, SN8 series mAbs will have good potential for the diagnosis and therapy of human diseases involving immunological functions as well as for the immunological manipulation of human B cells, e.g., inducing immune unresponsiveness.

BRIEF DESCRIPTION OF THE INVENTION

The invention comprises leukemia lymphoma reactive monoclonal antibodies directed toward individually different epitopes of the same antigen molecule which, relative to normal peripheral blood cells, strongly reacts with one or more leukemia lymphoma cell specimens from the group consisting of B prolymphocytic leukemia cells, B non-Hodgkin's lymphoma cells, B chronic lymphocytic leukemia cells, B hairy cell leukemia cells, and B acute lymphoblastic leukemia cells.

More particularly, three new IgG1-$\kappa$ monoclonal antibodies (mAbs), termed SN8, SN8a and SN8b, were generated by the use of an unconventional approach, i.e., utilizing an isolated B PLL antigen preparation to immunize mice. These mAbs, particularly SN8, showed a highly selective reactivity to B PLL and B non-Hodgkin's lymphoma among various human leukemia-lymphoma specimens tested, e.g., SN8 was capable of effectively distinguishing B PLL from B CLL as well as from HCL cell specimens. SN8 may be produced by hybridoma cell line 3A2–2E7 and clones thereof, SN8a may be produced by hybridoma cell line 3B3–1D2 and clones thereof and SN8b may be produced by hybridoma cell line Q6–1D5 and clones thereof. It is understood that the monoclonal antibodies of the invention are intended to include reactive fragments thereof, including F(ab')$_2$, Fab' Fab Fv, Fd' and Fd.

The invention further includes a diagnostic kit comprising monoclonal antibodies of the invention within a package.

The invention further comprises monoclonal antibodies which are directly or indirectly attached or complexed with a compound having a site suitable for attachment or complexing therewith which compound is selected from the group consisting of drugs, toxins or fragments thereof, growth suppressing biological response modifiers, enzymes, liposomes, radioactive agents and antibodies.

The invention also includes the methods for using the monoclonal antibodies for detecting and treating leukemia/lymphoma disease, as well as methods for preparation of the monoclonal antibodies and kits containing the same are also within the scope of the invention.

Finally, the invention also relates to the isolation and chemical identification of the human homologues of the murine mb-1 and B29 proteins of B cell antigen receptor complex. The amino-terminal amino acid sequences of the mb-1 and B29 gene products were determined using the antigen which was isolated using the monoclonal antibody SN8.

BRIEF DESCRIPTION OF THE FIGURES

FIG. 2 FACS analysis of SN8 reactivity with various human cells. Target cells were allowed to react with SN8 or an isotype-matching control mouse IgG (MOPC 195variant; IgG1-κ) and stained with fluorescence-conjugated F(ab')$_2$ of sheep anti-mouse Ig antibodies. The three bone marrow specimens shown were obtained from three different ALL patients in remission and mononuclear cells were isolated for use in the test. The three B cell specimens were individually isolated from the peripheral blood of three healthy donors. The B PLL and B CLL specimens were uncultured cell specimens. The fluorescence intensity is on a log scale.

FIG. 5 Competitive binding between mAbs to SN8 antigen on BALL-1 cells as measured by a cellular RIA. BALL-1 cells were incubated with serial dilutions of individual SN8 series mAbs or an isotype-matching control IgG for 1 h at 4° C. $^{125}$I-SN8 was then added, and the incubation was continued for an additional 1 h. Abscissa is ng of the purified SN8 series mAbs and control IgG. Radioactivity of $^{125}$I—SN8 bound to BALL-1 was in the range between 5.7 and 6.1×10$^3$ cpm when BALL-1 was preincubated with 10$^2$ to 10$^3$ ng of the control IgG or SN8b. The radioactivity was 331 and 190 cpm, respectively, when BALL-1 was preincubated with 10$^3$ ng of SN8 or SN8a.

FIG. 8 Western blot analysis of the SN8 antigen purified from BALL-1 cells by immunoaffinity chromatography.

Proteins recognized by SN8 were visualized on Kodak X-OMAT AR film using enhanced chemiluminescence (Amersham). The SN8 column eluate was examined on 8% SDS-polyacrylamide gels under nonreduced conditions (A) or after reduction with 0.1M DTT (B) (see Materials and Methods for details). Arrows indicate SN8 antigen specific bands. BioRad $M_r$ marker proteins were used as references and indicated in kD.

Figure 9:
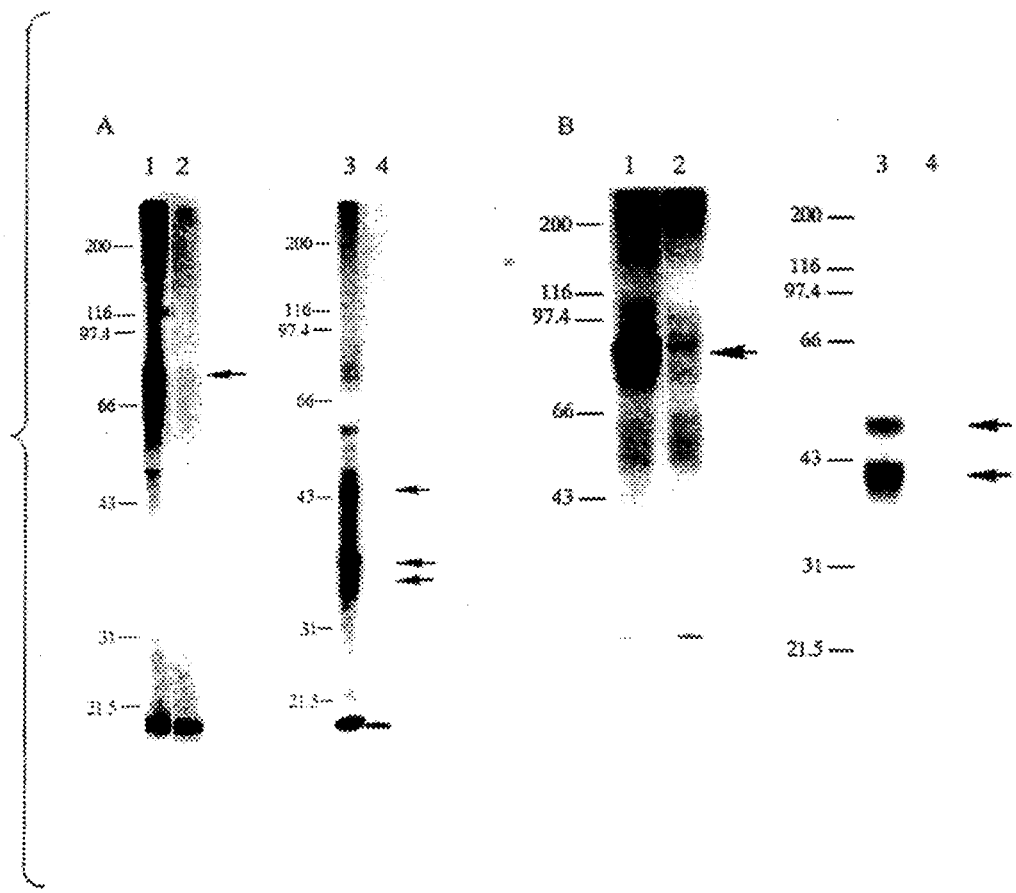

FIG. 9 Radioimmunoprecipitation of the SN8 antigen from a $^{125}$I-labeled antigen preparation from BALL-1 (panel A) and a $^{125}$I-labeled B PLL antigen preparation (panel B). An isotype-matched murine IgG (IgG1-κ) was used as a control against SN8 (lanes 2 and 4 in panels A and B). The immunoprecipitates were unreduced (lanes 1 and 2 in panels A and B) or reduced with DTT (lanes 3 and 4 in both panels) before they were subjected to SDS-PAGE. Arrows depict specifically immunoprecipitated proteins which were visualized by autoradiography. $M_r$ marker proteins (BioRad) are indicated in kD.

Figure 10:
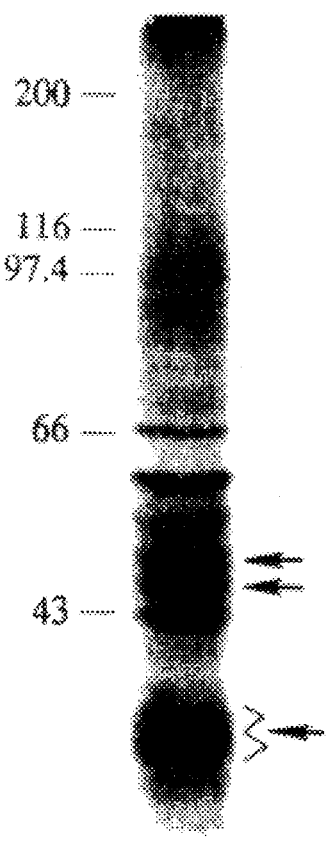

FIG. 10 Coomassie Blue visualization of the immunoaffinity purified SN8 antigen. The SN8 antigen was purified from detergent lysate of BALL-1 cells by repeated immunoaffinity chromatography. The sample was concentrated, reduced with DTT, subjected to SDS-PAGE, and transferred to a PVDF membrane by electroblotting (see Materials and Methods for details). The transferred proteins were visualized by staining with Coomassie Blue R-250. The arrows indicate the protein bands containing the human mb-1 protein and B29 protein, respectively, as revealed by amino-terminal amino acid sequence analyses. The diffuse 37 kD B29 protein band was divided into two portions as indicated in the figure and separately analyzed by amino acid sequencing. An identical amino-terminal amino acid sequence was obtained from the two samples by the sequence analyses.

FIG. 11 Amino-terminal amino acid sequences of the human B29 and mb-1 protein, Ala-Arg-Ser-Glu-Asp-Arg-Tyr-Arg-Asn-Pro-Lys-Gly-Ser-Ala-Xaa-Xaa-Arg, Sequence ID 1 and Leu-Trp-Met-His-Lys-Val-Pro-Ala-Ser-Leu-Met-Val-Ser-Leu-Gly-Glu-Asp-Ala-His-Phe, Sequence ID 2 respectively, are shown. These sequences may be compared to amino-terminal sequences of mouse B29 and mb-1 proteins wherein it is found that upon alignment a number of the human and mouse residues align. In particular five amino acid residues between the. B29 human and mouse proteins align and nine amino acid residues between the mb-1 human and mouse proteins align at locations indicated by underlined amino acids.

DETAILED DESCRIPTION AND PREFERRED EMBODIMENT OF THE INVENTION

Monoclonal Antibodies SN8, SN8a AND SN8b

Three new IgG1-κ monoclonal antibodies (mAbs), termed SN8, SN8a and SN8b, were generated by the use of an unconventional approach, i.e., utilizing an isolated B PLL antigen preparation to immunize mice. These mAbs, particularly SN8, showed a highly selective reactivity to B PLL and B non-Hodgkin's lymphoma among various human leukemia-lymphoma specimens tested, e.g., SN8 was capable of effectively distinguishing B PLL from B CLL as well as from hairy cell leukemia (HCL) cell specimens.

The cell surface antigen defined by the three mAbs was determined to be a covalently-linked heterodimeric glycoprotein complex (gp49/40) consisting of a 49,000 dalton component chain) and a 40,000 dalton component (β chain) and was subsequently identified as the human homologues of the murine mb-1 and B29 gene products. Epitope comparison showed that the epitope defined by SN8 (SN8 epitope) is in close proximity to SN8a epitope but in a distant position from SN8b epitope. Western blot analysis showed that both SN8 and SN8a epitopes are on the β chain, but SN8b epitope was not detected on either the α or the β chain of the reduced antigen in the same analysis. Binding of either SN8 or SN8b to the cell surface gp49/40 did not cause significant down-regulation of the antigen expression whereas binding of SN8a to the antigen caused small (approximately 20%) decrease in the antigen expression.

Among the various normal peripheral blood cells, only B cells reacted with the SN8 series mAbs; these mAbs showed no significant reactivity against T cells, granulocytes, monocytes, erythrocytes and platelets. Minimal or no significant reactivity (0 to 2.6% among different specimens) was detected against normal bone marrow cells. Ricin A-chain conjugates of the three mAbs are all strongly effective for specific killing of SN8 antigen-expressing leukemia cells in the absence of any potentiators; furthermore, the addition of 10 mM $NH_4Cl$, a potentiator, enhanced strongly the cytotoxic activities of the SN8, SN8a and SN8b conjugates. Thus, each of the three mAbs was effectively internalized after binding to the cell surface antigen.

Materials and Methods

The abbreviations used herein are as follows: B, B-cell; HLL, human leukemia-lymphoma; PLL, prolymphocytic leukemia; NHL, non-Hodgkin's lymphoma; CLL, chronic lymphocytic leukemia; HCL, hairy cell leukemia; ALL, acute lymphoblastic leukemia; mAb, monoclonal antibody; RIA, radioimmunoassay; SDS-PAGE, sodium dodecyl sulfate polyacrylamide gel electrophoresis; RA, ricin A chain; FACS, fluorescence activated cell sorter; FITC, fluorescein isothiocyanate; LcH, Lens culinaris lectin; RCA, Ricinis communis lectin; Ig, immunoglobulin; WBC, white blood cell; PBL, peripheral blood lymphocytes; FBS, fetal bovine serum; HLA-DR, human major histocompatibility complex, D region-related; kD, kilodalton.

Cells.

Various established human cell lines were cultured in RPMI 1640 medium supplemented with 4 to 10% fetal bovine serum (FBS), penicillin (100 units/ml) and streptomycin (50 μg/ml) (Seon et al. "Monoclonal antibody that defines a unique human T-cell leukemia antigen" Proc. Natl. Acad. Sci. USA, 80: 845, 1983). Peripheral blood, bone marrow aspirates and lymph node specimens from cancer patients were obtained at the Roswell Park Cancer Institute clinics (Takeuchi et al. "Monoclonal antibody SN10 which shows a highly selective reactivity with human B leukemia-lymphoma and is effectively internalized into cells", Cancer Res. 51: 2985, 1991). Mononuclear and blast cells were isolated from the cell suspensions of these specimens by centrifugation on a Ficoll-Paque gradient. Normal (or nearly normal) bone marrow specimens were from patients who were in remission and had a morphologically normal bone marrow. Mononuclear cells were isolated from the bone marrow aspirates by Ficoll-Paque gradient centrifugation.

B cells, T cells, granulocytes, monocytes, erythrocytes and platelets of normal peripheral blood were isolated from buffy coat preparations of healthy volunteers (Haruta et al. "Distinct human leukemia-associated cell surface glycoprotein GP160 defined by monoclonal antibody SN6", Proc. Natl. Acad. Sci., USA, 83: 7898, 1986).

Reagents, Control mAb and Control IgG.

L-[$^3$H]leucine-free medium were purchased from ICN Biomedicals, Inc. (Irvine, Calif.) and GIBCO Laboratories (Grand Island, N.Y.) respectively. Ricin A chain (RA) was obtained from Inland Laboratories (Austin, Tex.). mAbs SN3 (Fukukawa et al. "New monoclonal antibodies SN3, SN3a and SN3b directed to sialic acid of glycoprotein on human non-T leukemia cells" *Exp Hematol* 14: 850, 1986) (anti-CD24), SN4 (Luo et al. "Establishment of ascitic tumor of human pre-B acute lymphoblastic leukemia in nonconditioned nude mice", *Cancer Res.*, 49: 706, 1989) (anti-CD9), SN5 (Matsuzaki et al. "Unique. epitopes of common acute lymphoblastic leukemia antigen detected by new monoclonal antibodies", *Cancer Res.*, 47: 2160, 1987) (anti-CD10), SN6 (anti-GP160), G4-3A7 (anti-HLA-DR) and B3-3D1 (anti-HLA class I) were previously generated in Applicants laboratory. Control murine IgG (MOPC 195variant; IgG1-κ) was prepared in Applicant's laboratory. mAbs directed toward Leu1(CD5), Leu4(CD3), Leu12(CD19), Leu16(CD20) and HLA-DR (monomorphic) were purchased from Becton Dickinson (Mountain View, Calif.). Anti-human immunoglobulin λ chain mAb was obtained from AMAC, Inc. (Westbrook, Me.).

Fluorescein isothiocyanate (FITC)-labeled $F(ab')_2$ fragments of goat anti-human immunoglobulin (Ig) chain (each of κ, λ, γ, α and μ chains) antibodies were purchased from TAGO, Inc. (Burlingame, Calif.).

Antigen Preparation from Leukemia Cell Membranes.

Antigen was prepared from the cell membranes of leukemia cells derived from a patient with B PLL.

The patient presented with clinical symptoms of typical B PLL, i.e., massive splenomegaly, no lymphadenopathy, marked lymphocytosis with over 90% prolymphocytes, and a high WBC count ($2 \times 10^5/mm^3$). The cell surface phenotype of the B PLL cells was Ig $\kappa^+$, Ig λ, $Ig\mu^+$, $Ig\gamma^-$, $Ig\alpha^-$, $CD3^-$, $CD5^-$, $CD9^+$, $CD20^+$, $CD24^+$, $GP160^-$ and $HLA-DR^+$. The results indicate that the malignant cells of the donor patient are relatively mature B cells derived from a monoclonal origin; the phenotype of the cells is consistent with that of B PLL cells.

The procedures for isolating the cell membrane antigen are based on a modification of Applicant's previously reported novel isolation system (Seon et al. "Human T cell leukemia antigens on the cell membranes: Purification, molecular characterization, and preparation of specific antisers", *J. Immunol*, 127: 2580, 1981). A brief description of the present isolation system is given as follows: Cell membranes were prepared from the leukemia cells and cell membrane antigens were solubilized by deoxycholate treatment. The solubilized antigens were fractionated by affinity chromatography on serially connected columns of *Lens culinaris* lectin (LcH) and *Ricinus communis* lectin (RCA). The LcH-bound and RCA-bound glycoconjugates (mostly glycoproteins) were individually eluted, combined and subjected to passive immunoaffinity chromatography. To this end, the combined glycoproteins were passed through three serially connected immunoadsorbent columns. These immunoadsorbents consisted of anti-HLA class I mAb (B3-3D1), anti-HLA-DR mAb (G4-3A7), and rabbit anti-normal human peripheral blood lymphocyte antibodies, all coupled to SEPHAROSE CL-4B a 2,3-dibromopropanol treated cross-linked agarose gel containing 4% agarose beads sold by Pharacia Biotech Inc., Piscataway, N.J., USA. Materials in the pass-through fractions were pooled and concentrated.

Generation of mAbs.

Monoclonal antibody was generated by immunizing two BALB/c mice with the isolated antigen preparation. Immunization of the mice was carried out as described previously (Seon et al., *Proc. Natl. Acad. Sci. USA*, 80: 845, 1983). Cell fusion, hybridoma screening, cloning and mAb class determination was then performed. In general, the procedure for preparing the monoclonal antibodies of the invention comprises the following steps:

(a) preparing the cell membranes from leukemia cells and cell membrane antigens by solubilizing by deoxycholate treatment;

(b) fractionating the solubilized antigens by affinity chromatography on serially;

(c) eluting the LcH-bound and RCA-bound glycoconjugates from step (b) individually;

(d) combining the individually eluted glycoconjugates of step (c);

(e) submitting the combined glycoconjugates of step (d) to passive immunoaffinity chromatography;

(f) pooling and concentrating the materials in the pass-through fractions obtained from step (e);

(g) immunizing mice or rats with the isolated antigen preparation obtained from step (f);

(h) fusing the immune spleen cells from the mice or rats with an appropriate myeloma cell line; and (i) cloning the desired hybridomas produced by step (g).

Cellular Radioimmunoassay (RIA) and FACS Analysis.

Details of the cellular RIA which was used for determining reactivity of mAbs with various cultured and uncultured cells were described previously (Seon et al. "Monoclonal antibody SN2 defining a human T-cell leukemia-associated cell surface glycoprotein", *J. Immunol.*, 132: 2089, 1984). It should be noted that Fc receptors on the target cells are blocked with human IgG during the assay. In selected cases, the reactivity of mAbs with various cell specimens was also determined by FACS analysis.

Radioimmunoprecipitation and Sodium Dodecyl Sulfate Polyacryamide Gel Electrophoresis (SDS-PAGE)

The PLL antigen preparation (see above) and a LcH-bound glycoprotein preparation of PLL cells were separately radiolabeled with $^{125}I$ using an Iodo-gen coated Minisorp tube. The two radiolabeled preparations were used separately for immunoprecipitation and SDS-PAGE. An autoradiograph was prepared by using Kodak X-OMAT AR film and X-Omatic intensifying screen (Matsuzaki et al. "Molecular nature of a cell membrane antigen specific for human T-cell acute lymphoblastic leukemia", *Cancer Res.*, 47: 4283, 1987).

Western Blot Analysis.

This analysis was performed as described by Inman et al. ("Characterization of Sequential immune complexes in infective endocarditis by Western blot analysis", *J. Immunol*, 133: 217, 1984). The PLL antigen preparation was unreduced or reduced for 1 hr with 50 mM dithiothreitol. Then, SDS was added to the sample at the final concentration of 0.05% and the sample was subjected to SDS-PAGE. The separated proteins in SDS-PAGE were transferred to nitrocellulose membranes (Schleicher & Schuell, Keene, N.H.) with 25 mM Tris-192 mM glycine buffer (pH 8.3) containing 10% methanol. After preincubation with 10% normal goat serum, the membranes were incubated with hybridoma ascites or control ascites diluted in 10 mM Tris-HCl buffer (pH 7.4) containing 0.9% NaCl and 5% bovine serum albumin (Tris-saline-BSA), or Tris-saline-BSA containing an isotype-matching control murine IgG (MOPC 195variant). The membranes were washed with 10 mM Tris buffer (pH 7.4) containing 0.9% NaCl and 0.05% NP-40 (Tris-saline-NP40), treated with $^{125}I$-labeled $F(ab')_2$ of affinity-purified goat anti-mouse IgG antibodies, and washed with Tris-saline-NP40. The membranes were dried and autoradiograph was prepared as described above.

Competitive Antibody Binding.

This assay was carried out to make a comparison among epitopes defined by SN8, SN8a and SN8b. The assay was performed following Applicant's previously described procedure (Matsuzaki et al. "Unique epitopes of common acute lymphoblastic leukemia antigen detected by new monoclonal antibodies", *Cancer Res.*, 47: 2160, 1987).

Determination of Antigen in the Plasma of Human Leukemia-Lymphoma (HLL) Patients and Healthy Control Donors.

A solid-phase RIA was used. MOPC 195variant and anti-human Ig λ chain mAb (IgG1) were included in the test as an isotype-matching negative and a positive control, respectively.

A titration experiment showed that, in the above solid-phase RIA, Applicant could detect SN8 antigen contained in as little as 0.1 μg of cell membrane glycoproteins from B PLL cells.

Antigenic Modulation.

Regulation of antigen expression by SN8, SN8a and SN8b was studied by incubating BALL-1 cells for varying times at 37° C. with an excess of the individual mAbs (Seon et al., "Human T-cell leukemia-associated cell surface glycoprotein GP37: Studies with three monoclonal antibodies and a rabbit antiserum", *Mol. Immunol.*, 23: 569, 1986). Isotype-matching control IgG (MOPC 195variant) and control mAb SN5 defining CD10 were included in the assay as a negative and a positive control. The antigen on the cells was determined by cellular RIA.

Preparation of Immunotoxin.

The purified mAbs and an isotype-matching control mouse IgG (MOPC 195variant) were individually conjugated to ricin A chain (Hara et al. "Efficient transplantation of human non-T-leukemia cells into nude mice and induction of complete regression of the transplanted distinct tumors by ricin A-chain conjugates of monoclonal antibodies SN5 and SN6", *Cancer Res.*, 48: 4673, 1988). The conjugates were purified by gel filtration on a calibrated SEPHACRYLS-300 column allyl dextran covalently cross-linked with N,N-methylene bis acrylamide sold by Pharmacia Biotech Inc. followed by affinity chromatography on a Blue SEPHAROSE column.

Determination of Cytotoxic Activities of Immunotoxins.

A protein synthesis inhibition assay was used to determine the in vitro cytotoxic activities of immunotoxins against HLL cells and control cells.

Results

Initial Characterization with mAbS.

In the present invention, mAbs were generated by immunizing two mice with an isolated leukemia antigen preparation (see Materials and Methods). Initial characterization of primary hybridoma cultures and cloned hybridomas was carried out by testing against normal human peripheral blood lymphocytes (PBL), PLL cells and selected human cell lines by means of a cellular RIA. Hybridoma clones 3A2-2E7 American Type Culture Collection (ATCC) deposit designation number HB11413, and 3B3-1D2, ATCC deposit designator number HB11411 derived from mouse 1 and Q6-1D5, ATCC deposit designator number HB11412 from mouse 2 produced IgG1-κ mAbs which showed a selective reactivity with PLL cells and some B HLL cell lines. These mAbs were designated SN8, SN8a and SN8b, respectively. The above deposits were all made with the American Type Culture Collection (ATCC), 12301 Parklawn Drive, Rockville, Md. 20852, on July 20, 1993.

In Table 1, the test results of these mAbs with 28 malignant and 2 EB-virus transformed human cell lines are summarized. Among the 28 malignant HLL and myeloma cell lines tested, SN8 series mAbs showed a significant reactivity with only 7 relatively mature B HLL cell lines, i.e., BALL-1, Daudi, SU-DHL-4, U689-M, Ramos, BALM-3 and BALM-5. Furthermore, these mAbs did not react with two EB virus-transformed nonmalignant cell lines tested. This restricted reactivity of SN8 series mAbs with cultured cell lines is consistent with the reactivity of these mAbs with fresh (uncultured) HLL cell specimens as described below.

Reactivity with Fresh (uncultured) HLL Cells.

Reactivity of SN8 series mAbs with uncultured HLL cell specimens was determined by a cellular RIA and, in selected cases, also by FACS analysis.

Figure 1A:
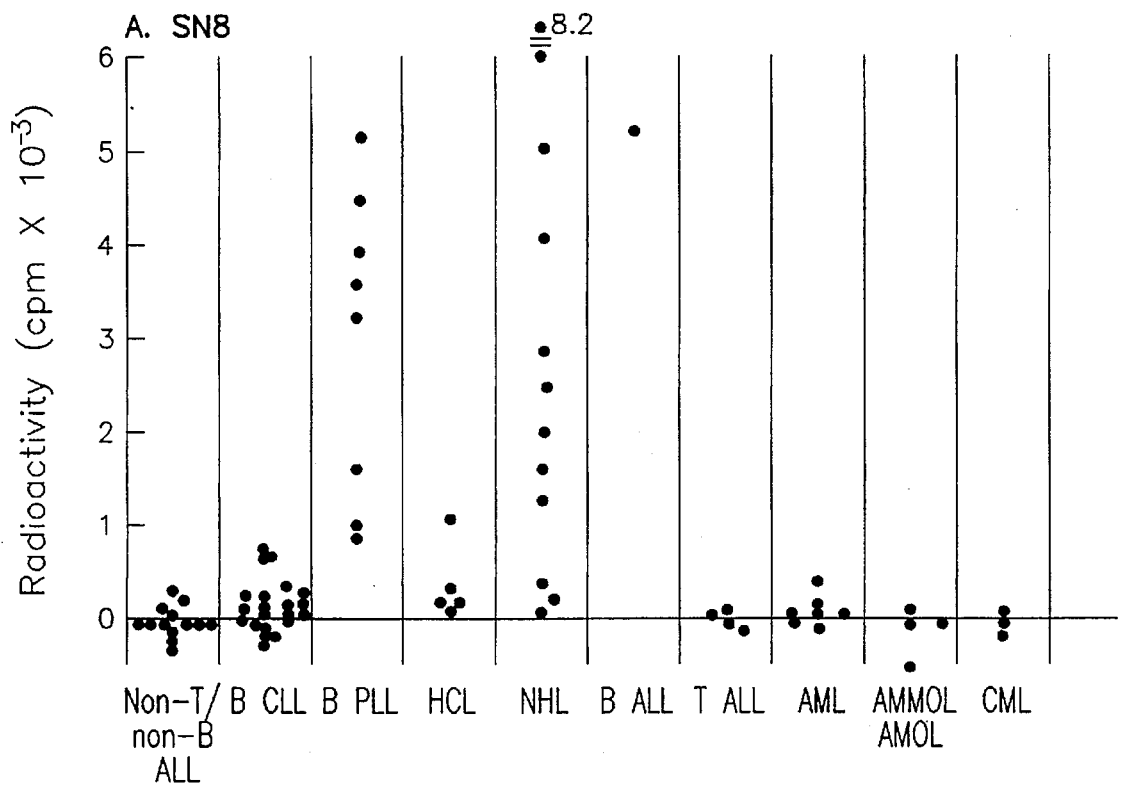
FIGS. 1A, 1B and 1C Reactivity of SN8 with fresh (uncultured) HLL cells as determined by a cellular radio-immunoassay (RIA). Individual cell specimens in panels FIGS. 1A, 1B and 1C were derived from peripheral blood, bone marrow aspirates or lymph nodes of 80, 60 and 44 different HLL patients, respectively. In the cellular RIA, three different controls were included with each test sample. One of these was control mouse IgG1 (10 µg/ml) in the hybridoma culture medium in place of the culture fluid of hybridoma SN8. Radioactivity counts of this control were subtracted from those of individual test samples in each test. The other two controls were a positive cell line and a negative cell line in place of the target cell specimen. Pre-B ALL was included in the group of non-T/non-B ALL in the figure. Abbreviations used in the figure: CLL, chronic lymphocytic leukemia; PLL, prolymphocytic leukemia; HCL, hairy cell leukemia; NHL, non-Hodgkin's lymphoma; ALL, acute lymphoblastic leukemia; AML, acute myelocytic leukemia; AMOL, acute monocytic leukemia; AMMOL, acute myelo-monocytic leukemia; CML, chronic myelocytic leukemia. The types of NHL specimens used are as follows: 2 diffuse small cleaved cell (SN8$^+$, SN8a$^+$, SN8b$^+$; SN8$^+$), 1 diffuse large cell (SN8$^+$, SN8a$^+$, SN8b$^+$), 2 diffuse mixed cell (SN8$^+$, SN8a$^+$, SN8b$^+$; SN8$^+$), 3 follicular small cleaved cell (SN8$^+$, SN8a$^+$, SN8b$^+$; SN8$^+$; SN8$^-$), 3 small lymphocytic (SN8$^-$, $^{SN}$8a$^-$, SN8b$^-$; SN8$^+$; SN8a$^+$; SN8$^-$, SN8a$^-$) and 1 follicular mixed cell (SN8$^+$) lymphoma.
Figure 1B:
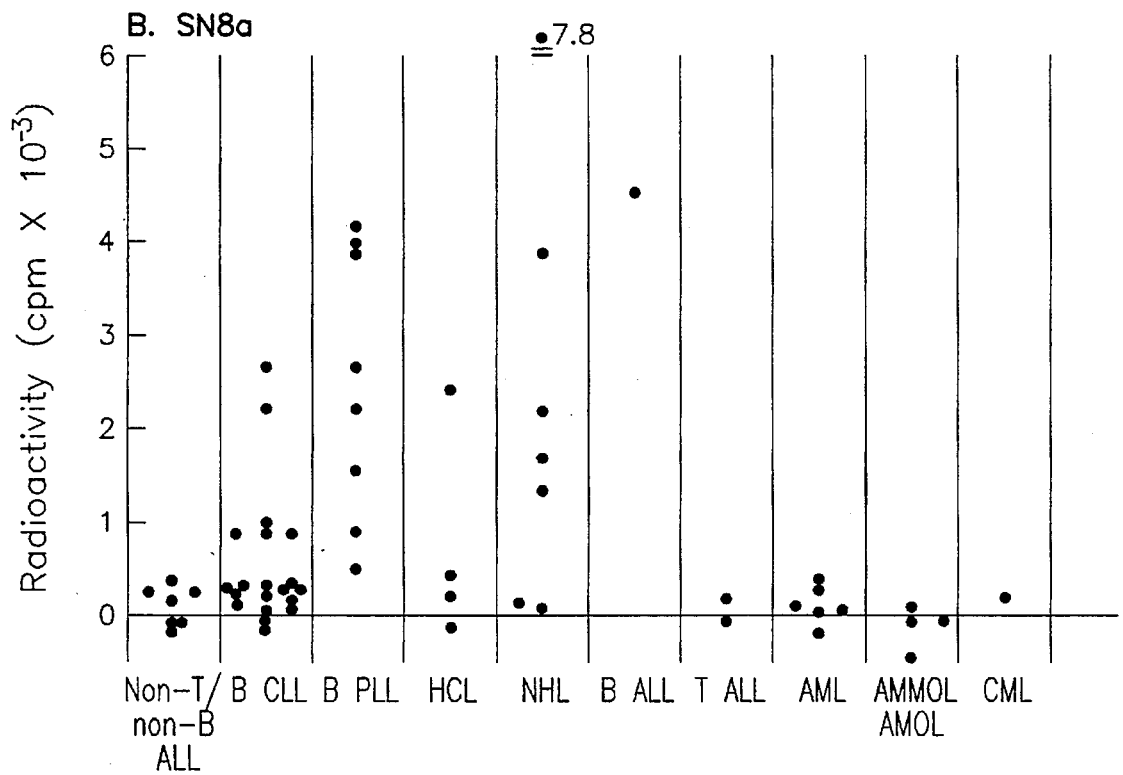
Figure 1C:
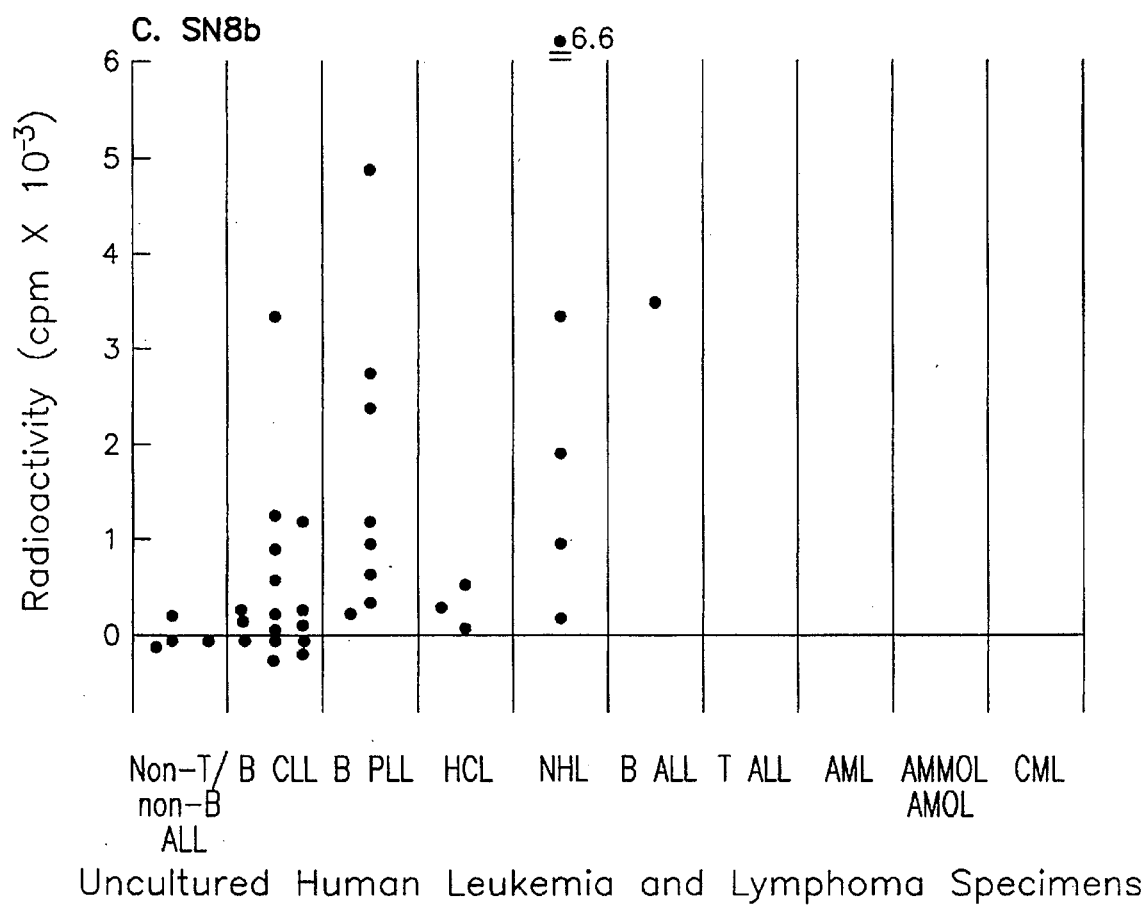

The results of a cellular RIA with SN8 and uncultured HLL cell specimens from 80 different HLL patients are summarized in FIG. 1. SN8 showed significant reactivity with all of the 8 B PLL, 9 of the 12 B NHL, the one B ALL, and one of the 5 hairy cell leukemia specimens tested. SN8 did not show significant reactivity with any of the specimens of non-T/non-B ALL, T ALL and myeloid/monocytic leukemias. Among the 23 B CLL specimens tested, only 3 showed weak but significant reactivity with SN8. Thus, SN8 shows a selective reactivity with PLL compared to CLL and hairy cell leukemia which are both closely related to PLL in the differentiation pathway of B cell ontogeny. The results of a cellular RIA were supported by FACS analysis, some of which are presented in FIG. 2 where over 90% of a PLL cell specimen reacted with SN8 whereas virtually none of the cells of the two CLL specimens were reactive.

The reactivities of SN8a and SN8b with uncultured cell specimens of 60 and 44 HLL patients, respectively, were tested by a cellular RIA. The results are presented in FIG. 1B and 1C. SN8a and SN8b showed a selective reactivity with B PLL and B NHL samples as SN8 did. However, these mAbs reacted with higher percentages (i.e., 30.0 and 31.3%, respectively) of CLL samples compared to SN8 (13.6%). Thus, the degree of PLL selectivity of these mAbs is less than that of SN8.

Reactivity with Uncultured Normal Cells.

B cells, T cells, monocytes, granulocytes, erythrocytes and platelets were isolated from the peripheral blood of three healthy donors and tested for reactivity with SN8 series mAbs by a cellular RIA. These mAbs showed a moderate reactivity with B cell specimens but no significant reactivity with other cell specimens. Therefore, the reactivities of SN8 series mAbs with B cells were further tested by FACS analysis. The FACS analysis results of SN8 are shown in FIG. 2. A subpopulation (6.0, 17.4 and 24.2%, respectively) of the B cell preparations derived from the three different donors reacted with SN8 (FIG. 2D, E and F). Two (Nos. 1 and 3) of these B cell preparations were tested for their reactivities with an anti-HLA-DR mAb (monomorphic; Becton Dickinson) by FACS analysis. The test showed that 53.4 and 74.2%, respectively, of the B cell preparations reacted with the anti-HLA-DR mAb. These two B cell preparations were also tested for their reactivities with SN8a and SN8b by FACS analysis. These mAbs reacted with 11.2 and 7.5%, respectively, of No. 1 sample as well as 23.0 and 13.5%, respectively, of No. 3 sample.

To further characterize the specificity of the mAbs, SN8 series mAbs were tested for their reactivities with normal (or nearly normal) bone marrow specimens by a cellular RIA and FACS analysis; these bone marrow specimens were obtained from 4 different ALL patients in remission. In the RIA, the reactivities of SN8 series mAbs with each of the 4 bone marrow samples (between 498 and 749 cpm) were slightly above the corresponding background values obtained by using an isotype-matching control IgG (281, 300, 201 and 356 cpm, respectively, against the 4 samples) whereas anti-HLA-DR mAb (Becton Dickinson) showed a strong reactivity with these bone marrow samples (7225, 221, 3581 and 5546 cpm, respectively).

In an additional study, FACS analysis was carried out with these bone marrow samples. The results of SN8 with 3 of the 4 samples are shown in FIG. 2 (panels A, B and C). Reactivity of SN8 with these 4 normal bone marrow specimens was not detectable (less than 1% for two specimens) or marginal (approximately 1 and 2.6%, respectively, for the two other specimens).

Molecular Nature of Antigen.

A leukemia antigen preparation from cell membrane glycoproteins of PLL cells (see Materials and Methods) was labeled with $^{125}I$ and used for immunoprecipitation with SN8 series mAbs and an isotype-matching control murine IgG (MOPC 195variant).

Figure 3:
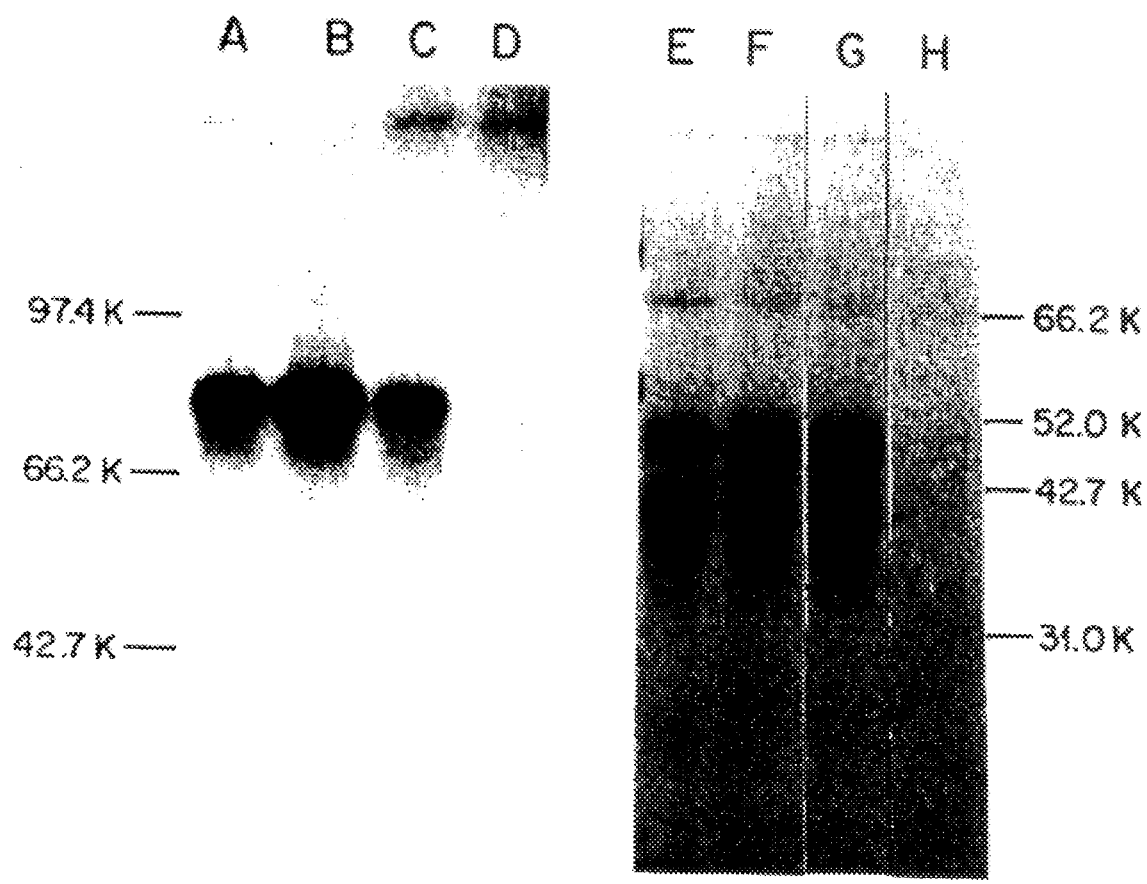
FIG. 3 SDS-PAGE of immunoprecipitates from a $^{125}$I-labeled PLL antigen preparation. In the immunoprecipitation, Applicants used SN8 (lanes A and E), SN8a (lane B and F), SN8b (lanes C and G) and control IgG (MOPC 195variant; lanes D and H). Samples were analyzed after being unreduced (lanes A, B, C and D) or reduced with dithiothreitol (DTT) (lanes E, F, G, and H). BioRad $M_r$ marker proteins ± the heavy chain of human IgG were used after reduction as references.

The immunoprecipitates were unreduced or reduced and analyzed by SDS-PAGE and autoradiographs were prepared. The results are shown in FIG. 3. Under unreduced conditions, each of the SN8, SN8a and SN8b immunoprecipitates showed a single component of approximately 81,000 daltons (lanes A, B and C), whereas no significant component was immunoprecipitated by the control IgG (lane D).

Under reduced conditions, each mAb immunoprecipitate showed two components of approximately 49,000 ($\alpha$ chain) and 40,000 ($\beta$ chain) daltons (lanes E, F and G), whereas the control IgG did not precipitate any significant component (lane H). Therefore, the antigen defined by the SN8 series mAbs consists of two polypeptide chains covalently linked by disulfide bond(s).

Epitope Study by Western Blot Analysis.

Figure 4:
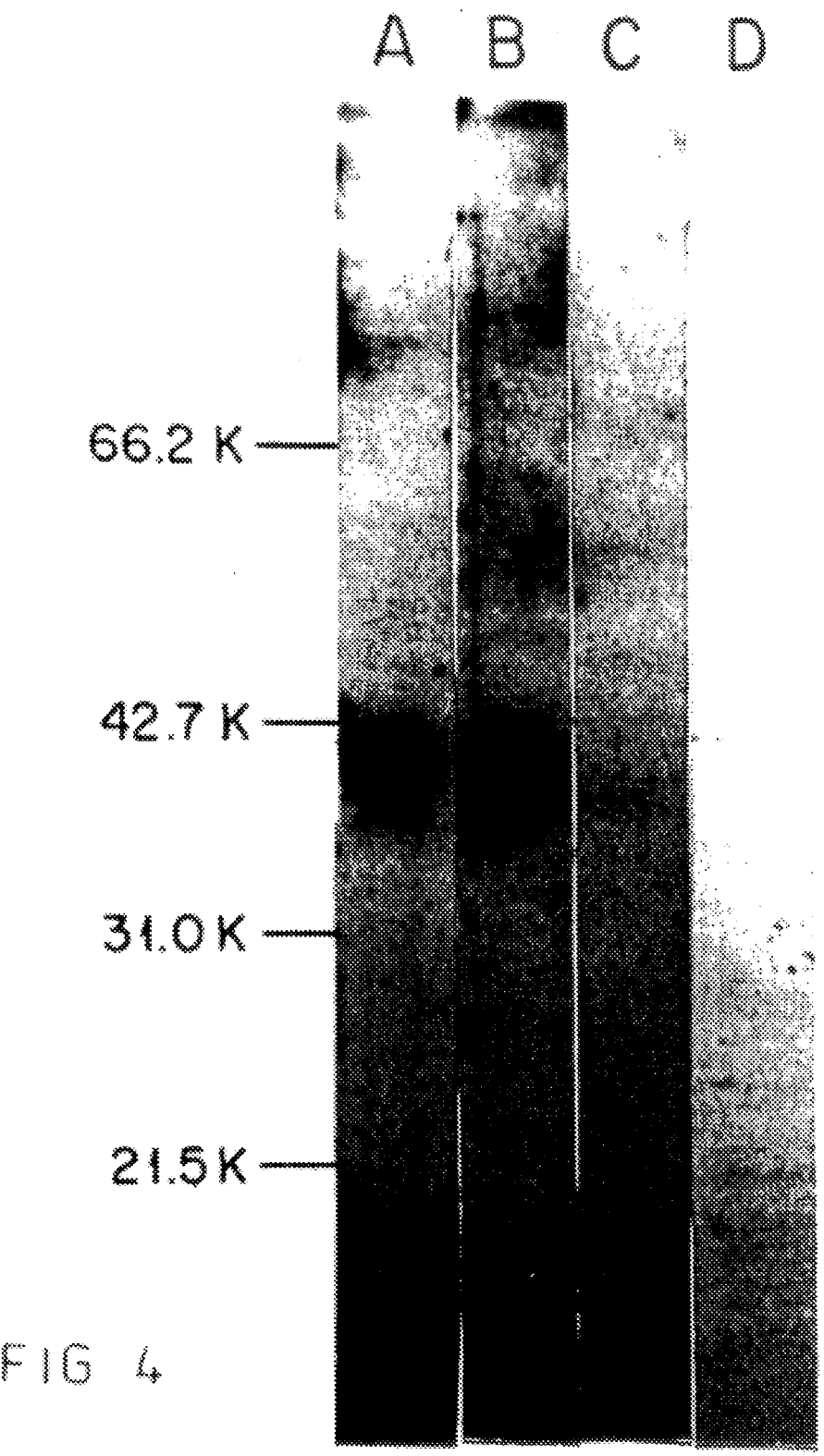
FIG. 4 Western blot analysis of the epitopes defined by SN8 series mAbs. A leukemia antigen preparation was reduced with 50 mM dithiothreitol and subjected to SDS-PAGE. The separated proteins in the gels were transferred to nitrocellulose membranes. After blocking with normal goat serum, the membranes were incubated with SN8 (lane A), SN8a (lane B), SN8b (lane C) or control IgG (lane D). The membranes were further treated with $^{125}$I-F(ab')$_2$ of affinity purified goat anti-mouse IgG antibodies. The marker proteins (shown in K daltons) are described in the legend to FIG. 3 except for soybean trypsin inhibitor (21.5K).

The assay was carried out after reducing the antigen preparation to determine the component of the antigen with which the SN8 series mAbs react (FIG. 4). Both SN8 and SN8a were shown to bind to the 40 kilodalton (kD) component ($\beta$ chain) of the SN8 antigen whereas SN8b did not bind to either component. When the assay was carried out with an unreduced sample, both SN8 and SN8a were found to bind strongly to the intact dimer antigen whereas SN8b bound to the antigen only very weakly. The results show that epitopes defined by SN8 and SN8a reside on the $\beta$ chain of the antigen, but SN8b epitope was probably perturbed or damaged under the experimental conditions used for treating the sample (see Materials and Methods).

Competitive Antibody Binding.

Figure 5:
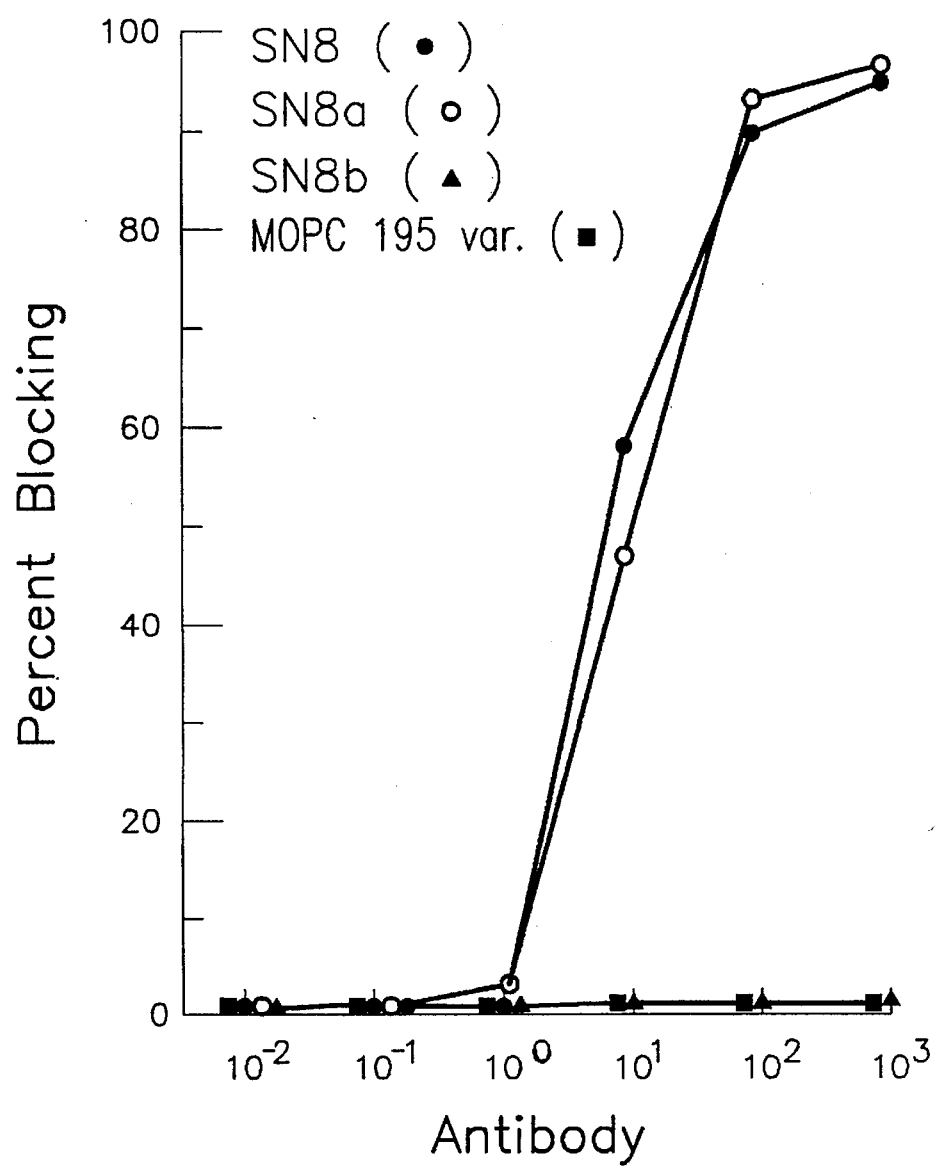

A competitive binding assay was carried out to compare the epitopes defined by SN8 series mAbs (FIG. 5). Preincubation of the SN8 antigen-expressing BALL-1 cells (see Table 1) with SN8 or SN8a completely blocked the subsequent binding of $^{125}I$-SN8 at the maximum. However, preincubation with SN8b or an isotype-matching control murine IgG did not inhibit the $^{125}I$-SN8 binding at all. These results indicate that the epitopes defined by SN8 and SN8a are in close proximity to each other but distant from the epitope defined by SN8b. These results are consistent with the above finding that both SN8 and SN8a bound to the same component ($\beta$ chain) in the Western immunoblotting.

Determination of Circulating Antigen in the Plasma of HLL Patients.

Circulating antigen in the plasma of patients may bind an administered mAb and thereby inhibit the therapeutic efficacy of the administered mAb and immunoconjugate. Therefore, Applicant tested for circulating SN8 antigen in the plasma of HLL patients and healthy individuals (control) by using mAbs SN8, SN8a and SN8b and a solid phase RIA. No significant amount of SN8 antigen was detected in any of the plasma samples derived from 7 different B NHL patients and 5 different B CLL patients. Similarly, no significant SN8 antigen was detected in the plasma samples derived from 5 different healthy individuals.

Regulation of Antigen Expression.

Figure 6:
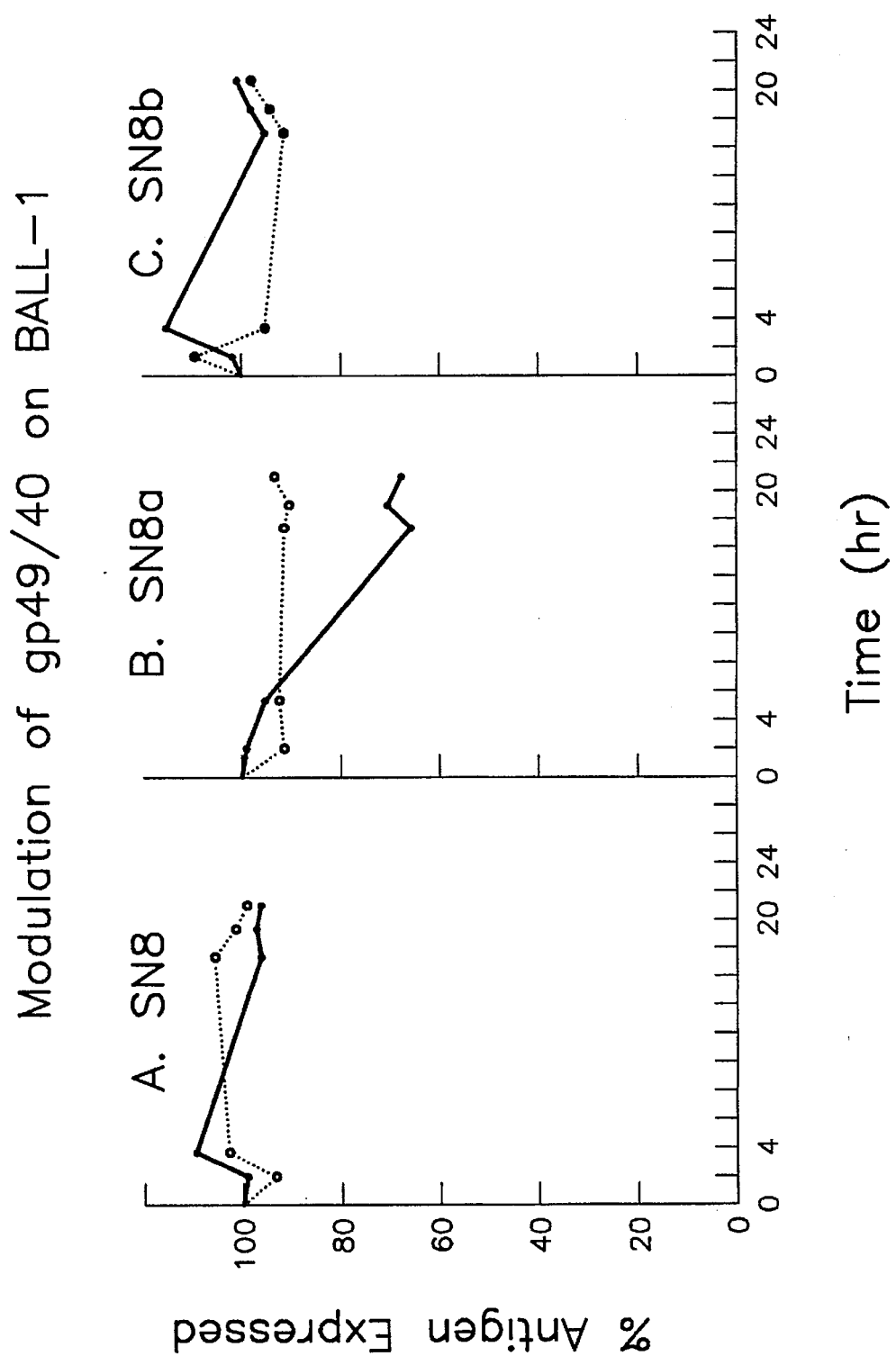
FIG. 6 Regulation of gp49/40 expression on BALL-1 which has been incubated with SN8, SN8a or SN8b. BALL-1 was incubated with an excess of purified mAb SN8, SN8a or SN8b (solid circles) or an isotype-matching purified control IgG (open circles) for varying periods of time. gp49/40 on the incubated cells was determined by a cellular RIA.

Binding of antibody to a cell surface antigen may induce antigenic modulation (Ritz et al. "Modulation of human acute lymphoblastic leukemia antigen induced by monoclonal antibody in vitro" *J. Immunol.*, 125: 1506, 1980) and down-regulation of antigen expression which may make antigen-targeting by antibody difficult. In the present invention, Applicant tested the effect of binding of SN8, SN8a and SN8b to BALL-1 on the expression of the SN8 antigen. Binding of either SN8 or SN8b to the cell surface SN8 antigen did not cause significant down-regulation of antigen expression whereas binding of SN8a to the antigen caused small (approximately 20%) decrease in the antigen expression (FIG. 6).

Nevertheless, all the SN8 series mAbs are effectively internalized into the HLL cells after binding as demonstrated by the effective killing of the HLL cells by the RA conjugates of these mAbs (see below).

Specific Killing of HLL Cells by RA Conjugates of mAbs.

Figure 7:
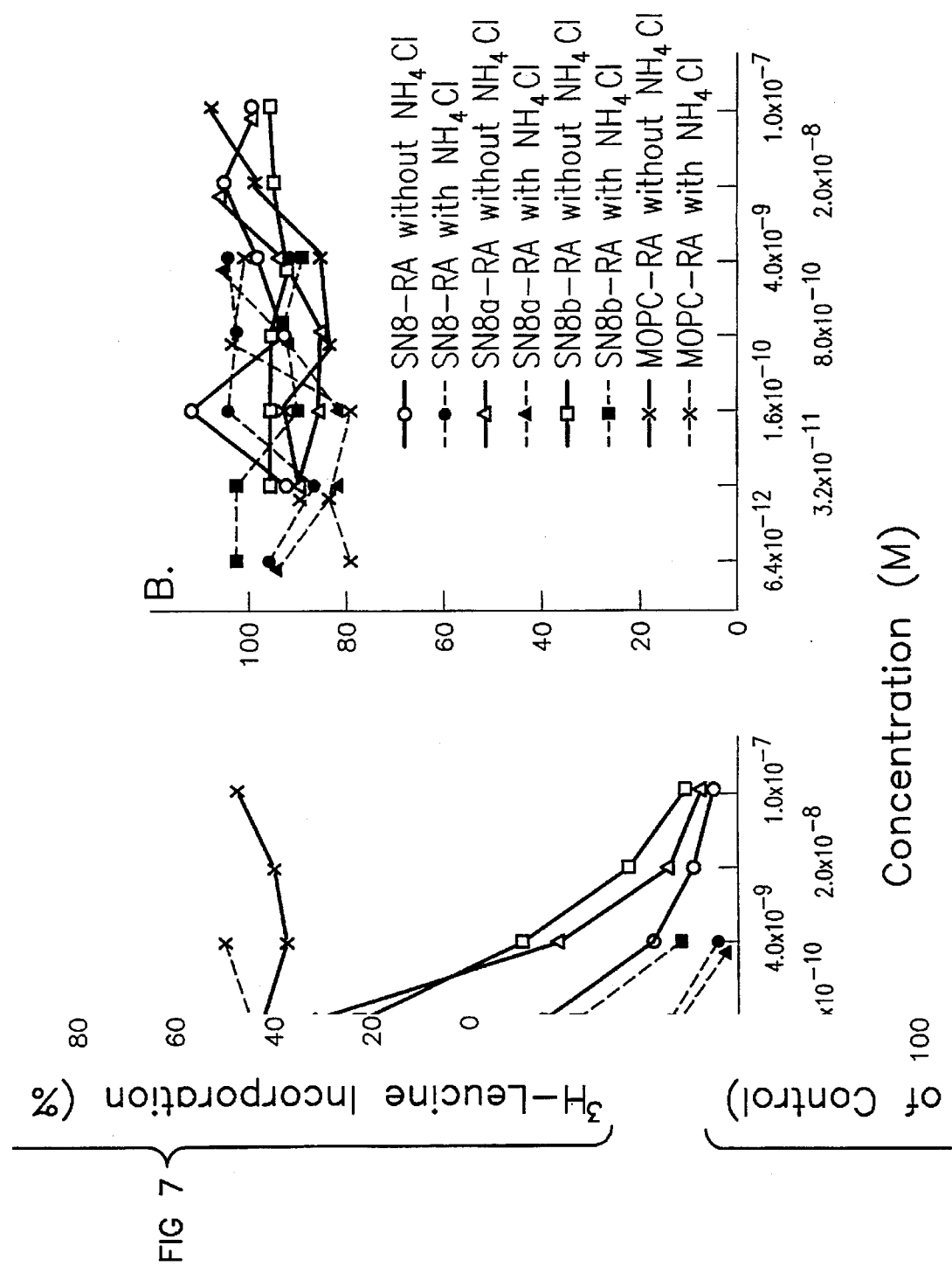
FIG. 7 Cytotoxic activities of RA conjugates of SN8 series mAbs as measured by a protein synthesis inhibition assay. BALL-1 (panel A) and gp49/40-negative MOLT-4 (control; panel B) were incubated with varying concentrations of individual SN8 series conjugates and a control conjugate in leucine-free medium for 24 h in the absence (solid lines) or presence (broken lines) of 10 mM NH$_4$Cl, a potentiator. The cells were pulsed with $^3$H-leucine and incubated for 4 h. The pulsed cells were harvested on glass fiber filters using a multiple semiautomatic cell harvester (type 7010; Skatron Inc., Sterling, Va.) and the 3H radioactivity was determined in a liquid scintillation spectrometer. Protein synthesis in the conjugate-treated cells is expressed as the percent of [$^3$H]leucine incorporated into control cells not exposed to conjugate. SN8-RA, SN8a-RA, SN8b-RA and control conjugate are indicated by circles, triangles, squares and X, respectively, in the figure.

Cytotoxic activities of RA conjugates of SN8, SN8a, SN8b and an isotype-matching control IgG were tested against the SN8 antigen-expressing BALL-1 and the SN8 antigen-negative control MOLT-4 cells in the absence or in the presence of 10 mM $NH_4Cl$, a potentiator. The results are shown in FIG. 7. In the absence of any potentiators, SN8-RA could inhibit the protein synthesis of BALL-1 for 50% of the control at a concentration of $5.0 \times 10^{-10}M$. The 50% inhibitory concentrations ($IC_{50}$) of SN8a-RA and SN8b-RA against BALL-1 were $2.6 \times 10^{-9}$ and $3.0 \times 10^{-9}M$, respectively (solid lines in FIG. 7A). However, the three RA conjugates did not inhibit the protein synthesis of control MOLT-4 cells at any of the concentrations tested (FIG. 7B). $NH_4Cl$ (10 mM) enhanced the cytotoxic activities of immunotoxins against BALL-1 but not against MOLT-4. $IC_{50}$ of SN8-RA, SN8a-RA and SN8b-RA against BALL-1 were $1.0 \times 10^{-10}$, $1.2 \times 10^{-10}$ and $4.8 \times 10^{-10}M$, respectively, in the presence of 10 mM $NH_4Cl$ (broken lines in FIG. 7A).

The control RA conjugate (MOPC-RA) did not show significant cytotoxicity against either BALL-1 or MOLT-4 in the absence or in the presence of NH4Cl. In an additional test, RA conjugates of SN8, SN8a and SN8b were tested for cytotoxicity against Daudi, a lymphoma cell line (see Table 1). $IC_{50}$ of SN8-RA, SN8a-RA and SN8b-RA were $8.2 \times 10^{-10}$, $6.7 \times 10^{-10}$ and $2.4 \times 10^{-9}M$, respectively. The cytotoxic activities of these conjugates against Daudi were potentiated by $NH_4Cl$; $IC_{50}$ in the presence of 10 mM $NH_4Cl$ were found to be $3.1 \times 10^{-12}$, $4.9 \times 10^{-12}$ and $1.3 \times 10^{-11}M$, respectively.

These results show that each of the RA conjugates of the three mAbs SN8, SN8a and SN8b is effective in specific killing of the SN8 antigen-expressing HLL cells. Furthermore, these results indicate that each of the three mAbs is effectively internalized into target HLL cells after binding to the cell surface antigen.

Discussion

The epitope defined by new mAb SN8 is detected on malignant B cells with a restricted stage of maturation, as well as on a small population of normal blood cells in the peripheral blood of healthy individuals. SN8 reacted with all of the 8 B PLL specimens and 9 of the 12 B NHL specimens tested but not with most of B CLL, HCL and non-T/non-B ALL (including pre-B ALL) specimens tested (FIG. 1). In addition, SN8 reacted with the one uncultured B ALL specimen tested as well as with one of the two B ALL cell lines tested (FIG. 1 and Table 1). It appears that SN8 is capable of effectively discriminating B PLL from B CLL and HCL as well as from non-T/non-B ALL. Among the previously reported mAbs, mAbs defining FMC-7 (Zola, "The surface antigens of human B lymphocytes", *Immunol. Today,* 8: 308, 1987) and CD22 (Knapp et al. (eds): *Leucocyte Typing IV: White Cell Differentiation Antigens,* Oxford, England, Oxford University Press, 1989) appear to be able to discriminate B PLL from some cases of B CLL but not from HCL; it should be noted that molecular properties of the antigens defined by these mAbs are different from the antigen defined by SN8.

It is believed that B CLL, B PLL and HCL are closely related in the differentiation pathway of B cell ontogeny while non-T/non-B ALL derives from normal counterparts at earlier stages of B cell ontogeny by malignant transformation and clonal expansion. B ALL is closely related to B lymphomas (Magrath et al. "Bone marrow involvement in Burkitt's lymphoma and its relationship to acute B-cell leukemia" *Leukemia Res.,* 4: 33, 1979) and its phenotype corresponds to that of relatively mature B cells. B NHL consists of a heterogeneous group of malignant B cells with varying degrees of maturation but the normal counterparts in the majority of cases of B NHL appear to be relatively mature B cells (Jaffe, "The role of immunophenotypic markers in the classification of non-Hodgkin's lymphomas" *Seminars Oncol.,* 17: 11, 1990). Phenotypic and genetic analyses suggest that B PLL derives from normal counterparts by malignant transformation at a later developmental stage than B CLL. For instance, B PLL cells express higher density of cell surface Ig than B CLL cells. Furthermore, Luzzatto et al. reported that in most cases of B PLL, the malignant clone has both alleles of Ig heavy chain gene in a rearranged configuration, while in many cases of B CLL, only one allele of the gene is rearranged and the other is found in a germ line-like configuration ("DNA rearrangements of cell lineage specific genes in lymphoproliferative disorders" Prog. Hematol., 14: 303, 1986). Similarly to B PLL, HCL also appears to derive from the clonal expansion of a B cell at a later developmental stage than B CLL. Between HCL and B PLL, the normal counterparts of HCL are probably more mature than those of B PLL in the differentiation pathway of B cell ontogeny.

SN8 reacted well with B PLL but poorly with HCL, B CLL and non-T/non-B ALL (FIG. 1). Thus, the results indicate that SN8 defines an epitope which is associated with a relatively narrow range of B cell maturation. The epitopes defined by SN8a and SN8b appear to be associated with slightly wider ranges of B cell maturation than SN8 epitope.

Applicant would like to point out that the present mAbs were generated using an unconventional approach, i.e., by immunizing animals with an HLL antigen preparation rather than with intact HLL cells. Previously, Applicant developed a novel system for isolating immunologically active HLL associated cell membrane antigen mixtures (Seon et al. "Human T cell leukemia antigens on the cell membranes: Purification, molecular characterization, and preparation of specific antisers", *J. Immunol,* 127: 2580, 1981). In the present invention, this system was applied to isolating a B PLL associated cell membrane antigen preparation which was used for generating mAbs.

SN8 series mAbs appear to be different from those previously reported mAbs in the antibody specificity and/or in the molecular nature of the antigen defined. The SN8 antigen defined by the present mAbs appears to be different from any of the reported CD series antigens. Among the CD series antigens, CD72 shows some similarity to the SN8 antigen; CD72 is a heterodimer of 43,000 and 39,000 dalton components. However, besides the smaller molecular size of the heavier component of CD72 compared to the α chain (gp49) of SN8 antigen, there are distinct differences in the specificity between anti-CD72 mAb and SN8 series mAbs. For instance, anti-CD72 mAb reacted with 44% (7 of the 16 specimens tested) of non-T/non-B ALL specimens, all (3/3) of the HCL specimens, and NALM-6, a pre-B ALL cell line. In contrast, SN8 series mAbs did not react with any of the non-T/non-B ALL specimens tested (i.e., 0/13, 0/7 and 0/4, respectively, for SN8, SN8a and SN8b), did not react with the majority of the HCL specimens (1/5, 1/4 and 0/3, respectively), and did not react with NALM-6 (see FIG. 1 and Table 1).

As described above, anti-CD22 mAbs show some similarity to the novel SN8 series mAbs in their specificity. However, CD22 is a single polypeptide chain antigen with a molecular weight of 135,000.

Furthermore, Applicant's recent amino acid sequence studies revealed unequivocally that the two components (α and β chains) of the SN8 antigen are the novel human homologues of the murine mb-1 and B29 proteins, respectively, of the B cell antigen receptor complex.

The data presented here suggests the usefulness of SN8 series mAbs, particularly SN8, for diagnosis of HLL and follow-up of B PLL and B NHL. The data also suggests the usefulness of these mAbs for diagnosis and follow-up of normal B cells in patients with immunological disorders. Another important application of these mAbs may be their utilization as a specific delivery vehicle of a cytotoxic agent(s) to malignant and normal B cell targets (Vitetta et al. "Redesigning nature's poison to create anti-tumor reagents" *Science,* 238: 1098, 1987).

As an initial test for the utility of SN8 series mAbs for preparing immunoconjugates, these mAbs were conjugated with ricin A chain (RA), and the in vitro cytotoxic activities of the generated immunotoxins were determined. All of the three immunotoxins killed the SN8 antigen-expressing HLL cells effectively while showing no significant cytotoxicity against control cells. Thus, these immunotoxins showed specific cytotoxicity and each of SN8 series mAbs bound to the target antigen on HLL cells was effectively internalized into the cells. However, the binding of these mAbs to HLL cells did not cause (SN8 and SN8b) or caused only a small degree (SN8a) of down-regulation of antigen expression. These results may be explained by one recent finding that there is dynamic balance (or unbalance in some cases) between endocytosis and exocytosis-cell surface expression of an antigen on the cell surfaces (Luo et al. "Marked difference in the in vivo antitumor efficacy between two immunotoxins targeted to different epitopes of common acute lymphoblastic leukemia antigen (CD10): Mechanisms involved in the differential activities of immunotoxins", *J. Immunol.,* 145: 1974, 1990). Therefore, an antibody-bound antigen can be effectively internalized even when no modulation of the overall cell surface expression of the antigen is observed. No significant amount of circulating antigen was detected in the plasma of HLL patients or healthy individuals. Therefore, the initial studies with these new mAbs and their immunoconjugates appear to suggest the potential of these mAbs as delivery vehicles of cytotoxic agents to malignant and normal B cell targets.

Also, various antibody fragments can be made from mabs SN8, SN8a and SN8b using well known techniques (Parham et al., "Monoclonal antibodies: purification, fragmentation and application to structural and functional studies of class I MHC antigens" *J. Immunol. Meth.*, 53: 133–173, 1982).

Finally, according to this invention, genetically engineered chimeric antibodies or fragments thereof of SN8, Sn8a and SN8b can be directly or indirectly attached or complexed with a compound having a site suitable for attachment or complexing therewith which compound is selected from the group consisting of drugs, toxins or fragments thereof, growth suppressing biological response modifiers, enzymes, liposomes, radioactive agents, photodynamic agents and antibodies (BioTechniques, Vol. 4, No. 3: 214–220, 1986).

Human Homologues of the Murine mb-1 and B29 Proteins of B Cell Antigen Receptor Complex Binding of antigen to the antigen receptor on B cells initiates complicated cascades of signal transduction which may lead to proliferation, differentiation or programmed cell death of the B cells. Furthermore, cross-linking of the antigen receptor by anti-Ig antibodies results in rapid tyrosine phosphorylation of substrate proteins suggesting that the B cell antigen receptor belongs to a subgroup of the tyrosine kinase receptor family (Gold et al. "Stimulation of protein tyrosine phosphorylation by the B-lymphocyte antigen receptor", *Nature*, 345: 810, 1990).

It has been known for over 20 years that cell membrane immunoglobulins (mIgs) constitute antigen receptors on B cells (Pernis et al. "Immunoglobulins as cell receptors" *Ann. N.Y. Acad. Sci.* 190: 420, 1972). The isotype of mIg is IgM or IgM plus IgD on most B cells, but IgG, IgA or IgE can also be found on some B cells. Recent studies of Hombach et al. ("A novel 34 kD protein co-isolated with IgM molecule in surface IgM-expressing cells" *EMBO J.* 7: 3451, 1988; "Molecular components of the B-cell antigen receptor complex of the IgM class" *Nature*, 343: 760, 1990) and Campbell et al. ("B lymphocyte antigen receptors (mIg) are non-covalently associated with a disulfide-linked, inducibly phosphorylated glycoprotein complex", *EMBO J.* 9: 441, 1990) on a murine myeloma variant and murine normal B cells revealed that the mIgM is non-covalently associated with a disulfide-linked heterodimer consisting of a 32–34 kD and a 37–39 kD subunit. Subsequent studies by several investigators revealed that a similar mIg associated heterodimer exists on murine and human B cells; the subunits of this heterodimer were termed Ig-α and Ig-β, respectively (Cambier et al. "Membrane immunoglobulin and its accomplices: new lessons from an old receptor" *FASEB J.*, 6: 3207, 1992; Reth, "Antigen receptors on B lymphocytes", *Annu. Rev. Immunol.*, 10: 97, 1992). The mIg associated αβ heterodimer is believed to be important for signal transduction. Recently, murine Ig-α and Ig-β were identified as the products of mb-1 and B29 genes, respectively (Sakaguchi et al. "B lymphocyte lineage restricted expression of mb-1, a gene with CD3-like structural properties" *EMBO J.*, 7: 3457, 1988; Hermanson et al. "B29: A member of the immunoglobulin gene superfamily exclusively expressed on B-lineage cells" *Proc. Natl. Acad. Sci. USA*, 85: 6890, 1988; Hombach et al. "Identification of the genes encoding the IgM-α and Ig-β components of the IgM antigen receptor complex by amino-terminal sequencing" *Eur. J. Immunol*, 20: 2795, 1990). Most of the information about the structures and functions of the mIg associated heterodimer have been derived from studies of murine B cells and murine myeloma variants.

In this invention, Applicant has determined that the amino-terminal amino acid sequences of the two subunits of a disulfide-linked heterodimeric antigen that was isolated from human B leukemia cells using a mAb termed SN8, specific for an extracellular epitope of the Ig-β component of the heterodimer. These results clearly demonstrate that these subunits are the products of the human homologues of the murine mb-1 and B29 genes.

Materials and Methods

Additional abbreviations used herein are as follows: AEBSF, 4-(2-aminoethyl)-benzenesulfonylfluoride; CAPS, 3-(cyclohexylamino)-1-propanesulfonic acid; PVDF, polyvinylidene-difluoride; and DTT, dithiothreitol.

Antibodies, Cells and Reagents.

mAb SN8 was recently generated in Applicant's laboratory by an unconventional approach, i.e., immunizing mice with a glycoprotein antigen preparation isolated from B PLL cells rather than immunizing mice with intact cells. SN7 (Okazaki et al., "A new mAb reactive with human malignant and normal B cells", manuscript in preparation), B3-3D1 (anti-human MHC I mAb) and an isotype-matched (IgGl-κ) control murine IgG (MOPC 195variant) were also generated in Applicants laboratory. BALL-1, a B ALL cell line, was cultured in RPMI 1640 medium supplemented with 4% FCS, penicillin (100 units/ml) and streptomycin (50 µg/ml). BALL-1 expresses both mIgM-λ and mIgD-λ. Peripheral blood cells derived from a patient with B PLL were obtained at the Roswell Park Cancer Institute clinics. This B PLL cell specimen expressed mIgM-κ. AMINOLINK coupling gel, a 4% cross linked beaded agarose support activated to form aldehyde functional groups, sold by Pierce, Rockford, Ill., USA. Enhanced chemiluminescence (ECL) Western blotting detection reagents, and peroxidase-labeled goat anti-mouse Ig were obtained from Amersham (Arlington Heights, Ill.) and Boehringer-Mannheim (Indianapolis, Ind.), respectively. AEBSF, a new inhibitor of serine proteases, was purchased from Calbiochem (La Jolla, Calif.) while Trasylol and leupeptin were obtained from Sigma (St. Louis, Mo.).

Isolation of αβ Heterodimer from BALL-1.

$1.65 \times 10^{10}$ BALL-1 cells were lysed for 1 h at 4° C., with gentle shaking, in 160 ml of 20 mM Tris-HCl buffer, pH 8.0, containing 0.15M NaCl, 1% (vol/vol) Triton X-100, 1 mM iodoacetamide, Trasylol (100 KIU/ml), 1 µM leupeptin and 0.1 mM AEBSF. The lysate was centrifuged at 3,000× g for 20 min at 4° C. Sodium deoxycholate was added to the supernatant to a final concentration of 0.5% and the supernate was centrifuged at 150,000 ×g for 60 min at 4° C. The resulting supernate was applied to three serially connected immunoadsorbent columns. These immunoadsorbents consisted of MOPC 195variant (4 ml gel; 2.1 mg IgG/ml gel), anti-HLA class I mAb (B3-3D1) (5 ml gel; 3.7 mg IgG/ml gel), and mAb SN7 (6 ml gel; 3.3 mg IgG/ml gel), all coupled to (AMAINOLINK) coupling beaded gel (Pierce). The pass-through materials from the three immunoadsorbent columns were applied to two serially connected immunoadsorbent columns consisting of MOPC 195variant-agarose (4 ml gel; 2.1 mg IgG/ml gel) and mAb SN8-agarose (4 ml gel; 1.5 mg IgG/ml gel). The columns were washed with 20 mM Tris-HCl, pH 8.0, containing 0.15M NaCl and 1% (RENEX) polyoxyethylene (12) tridecyl ether, sold by ICI Americas Inc., Wilmington, Del. USA 30, a nonionic detergent. Then, the columns were disconnected and the materials bound to individual columns were separately eluted with 0.1M glycine-HCl buffer, pH 3.0, containing 0.5% (RENEX) 30 with the eluate immediately neutralized by collecting 2 ml fractions into tubes containing 120 µl of 1M Tris-HCl, pH 8.0. (RENEX) 30, which does not show significant optical absorbance at 280 nm, allows the fractionated proteins to be followed spectrophotometrically. The materials eluted from the SN8 column were subjected to a second immunoaffinity chromatography using the SN8 column.

Radioimmunoprecipitation and SDS-PAGE.

Protein samples were radiolabeled with $^{125}I$ by using IODO-GEN (Pierce)-coated Minisorp tubes. Immunoprecipitation of $^{125}I$-labeled αβ heterodimer from the radiolabeled samples was carried out using SN8 conjugated to (AMINOLINK) agarose or (PANSORBIN) suspension of *staphylococcus aureus* cells, sold by Calbiochem, San Diego, Calif., USA. which was coated with rabbit antimouse IgG and SN8. An isotype-matched (IgG-κ) control IgG (MOPC 195variant) or an isotype-matched irrelevant mAb (SN11 (Takeuchi et al., manuscript in preparation)) that was coupled to an appropriate matrix (AMINOLINK agarose or PANSORBIN) was used as controls.

Details of the procedure for immunoprecipitating radiolabeled antigens using PANSORBIN coated with rabbit anti-mouse IgG and an IgG1 mAb were previously described (Haruta et al. "Distinct human leukemia-associated cell surface glycoprotein GP160 defined by monoclonal antibody SN6" *Proc. Natl. Acad. Sci.*, USA, 83: 7898, 1986). The procedure for immunoprecipitating antigens using SN8-agarose is discussed below.

An aliquot of a radiolabeled sample is pretreated with an irrelevant mAb-agarose by incubating for 2.5 h in ice-water. The incubated mixture is centrifuged and the supernate was divided into 4 equal aliquots. Reaction tubes containing these aliquots were incubated with SN8-agarose (in duplicate) or MOPC-agarose (in duplicate) for 4 h in ice water and centrifuged. The resulting pellets were washed twice with Tris-HCl, pH 8.0, containing Trasylol (100 KIU/ml), 2 nM EDTA, 0.05% $NAN_3$, 0.1% BSA and 0.5% taurocholate (Tris-BSA-TC) and twice with Tris-BSA-RENEX (Tris-BSA containing 0.5% RENEX 30 instead of 0.5% taurocholate). The pellets were finally washed with 62.5 nM Tris-HCl buffer, pH 6.8. The radiolabeled antigens present in the washed immunoprecipitates were released from the agarose beads by boiling for 3 min in the presence of 2% SDS with or without 0.2M DTT. The released antigens were analyzed by SDS-PAGE.

Western Blot Analysis.

A recently reported procedure (Okazaki et al. "Three new monoclonal antibodies that define a unique antigen associated with prolymphocytic leukemia/non-Hodgkin's lymphoma and are effectively internalized after binding to the cell surface antigen" Accepted for publication in *Blood* and scheduled to appear in the Jan. 1st, 1993 issue) was modified and the modified procedure is briefly described. A sample in 20 nM Tris-HCl, pH 7.7, containing 0.5% taurocholate is mixed with an equal volume of sample treatment buffer and incubated for 1 h at 37° C.; the sample treatment buffer consists of 62.5 nM Tris-HCl, pH 6.8, 0.1% SDS, 10% glycerol and 0.006% bromophenol blue. For reduction of the sample, 0.2M DTT is included in the buffer. The separated proteins in SDS-PAGE are electroblotted in 10 nM CAPS, pH 11.0, containing 10% methanol to a PVDF membrane (Immobilon-P, Millipore), for 45 min at 500 mA. The membrane is incubated overnight at 4° C. in 0.01M PBS, pH 7.0, containing 1% nonfat dry milk (blocking buffer). From this point, all steps are carried out at room temperature. The blocked membrane is incubated for 1 h with SN8 ascites that was diluted 1,000 fold with blocking buffer containing 0.1% (TWEEN) 20-polyoxyethylene sorbitan monolaurate, sold by Sigma Chemical Company. The membrane is next washed three times (each wash for 10 min) with blocking buffer containing 0.5% (TWEEN) 20. Secondary antibody (horseradish peroxidase conjugated goat anti-mouse Ig antibodies) which was diluted 1,000 fold with blocking buffer containing 0.1% (TWEEN) 20 is added to the membrane and incubated for 1 h. Finally, the membrane is washed 6 times for 10 min each in 50 nM Tris-HCl, pH 8.0, containing 0.15M NaCl, 0.1% NP-40 and 0.05% (TWEEN) 20. Proteins recognized by SN8 are visualized on Kodak X-OMAT AR film using enhanced chemiluminescence (Amersham, Arlington Heights, Ill.) following the manufacturer's protocol.

Amino-terminal Amino Acid Sequence Determination.

The eluate from the SN8 immunoadsorbent column (see above) was placed in a Spectrapor dialysis tubing (MWCO 50,000) (Spectrum, Los Angeles, Calif.) and dialyzed against four daily changes of 20 nM Tris-HCl buffer, pH 8.0, containing 0.5% deoxycholate and Trasylol (25 KIU/ml) and two daily changes of 20 nM Tris-HCl buffer, pH 8.0, containing 0.5% taurocholate. The dialyzed sample was concentrated (20 to 30 fold) using a (CENTRICON)-30 microconcentrator with 30,000 molecular weight cutoffs, sold by Amicon, Inc. Samples were incubated for 3 h at room temperature with an equal volume of a modified SDS-PAGE sample treating buffer containing 4% SDS prior to gel electrophoresis. This sample treatment was necessary to minimize the problem (observed during SDS-PAGE) caused by the concentrated nonionic detergent. Ultrapure reagents and deionized, double-distilled $H_2O$ were used in the following experiments. The separating gels in SDS-PAGE were allowed to polymerize overnight at room temperature before being used, and thioglycolic acid (final 0.1 nM) was added to the upper gel running buffer in the SDS-PAGE. Reduced proteins separated in SDS-PAGE were transferred to a PVDF membrane using the same conditions as those described above in Western blot analysis except that 0.1 nM thioglycolic acid was included in the CAPS transfer buffer. After electroblotting, the membrane was washed, stained with Coomassie Blue R-250, and destained as described by Matsudaira ("Sequence from picomole quantities of proteins electroblotted onto polyvinylidene difluoride membranes" *J. Biol. Chem.*, 262: 10035, 1987). The stained protein bands were individually cut out with a clean razor. $NH_2$-terminal amino acid sequencing of the stained protein was performed with a protein sequencer model 477A with a blot cartridge (Applied Biosystems, Foster City, Calif.) according to the manufacturer's program, BLOTT-1. The sequences obtained were compared with all reported sequences in the Gen Bank database (Release 73.0, September 1992).

Results and Discussion

Figure 8:
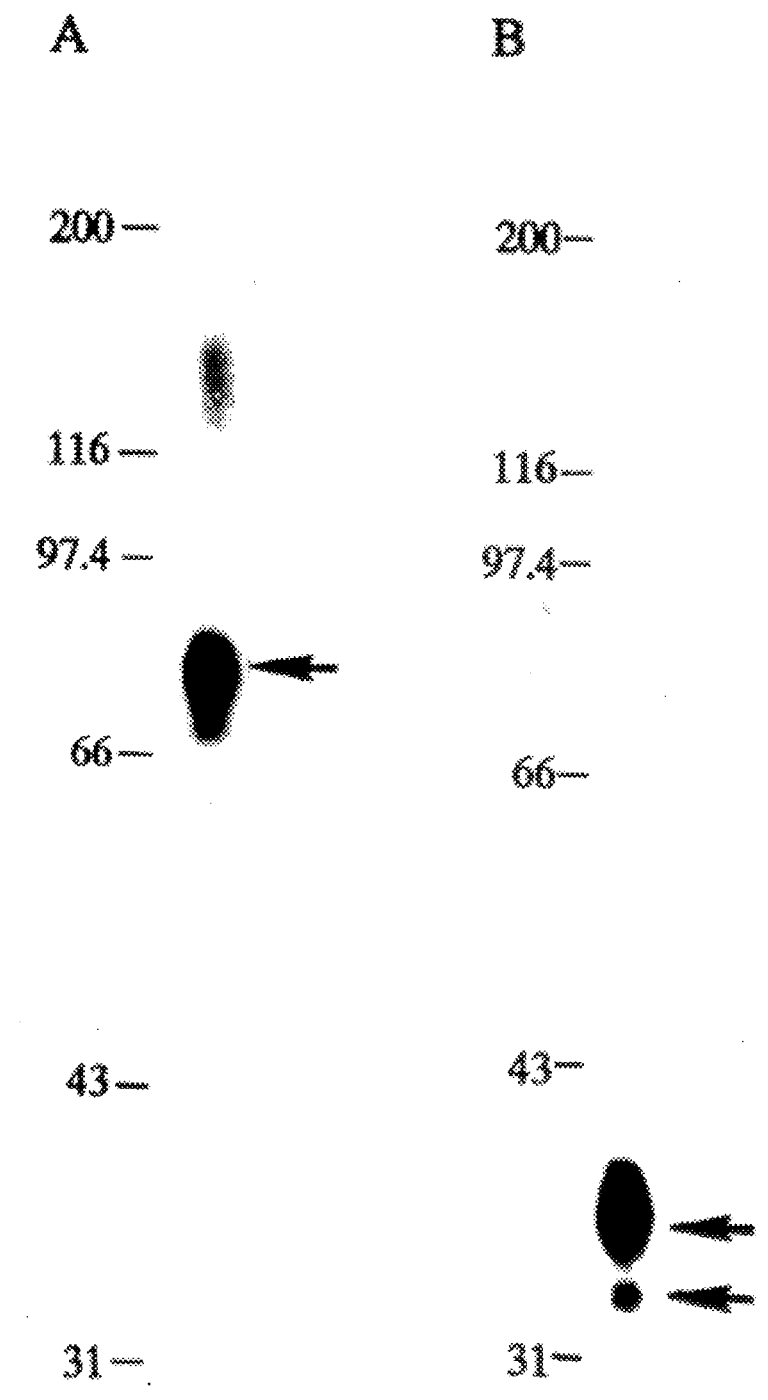

An antigen preparation was isolated from BALL-1 human B leukemia cells by detergent lysis and immunoaffinity chromatography (see Materials and Methods for details). The acid eluate from SN8-column was analyzed by Western blotting and the result is shown in FIG. 8. Under unreduced conditions, the antigen detected by SN8 had an approximate $M_r$ of 80 kD (FIG. 8A). Under reduced conditions, SN8 reacted with a diffuse major component of 37 kD and a minor component of 33 kD (FIG. 8B).

The SN8-column eluate was radiolabeled with $^{125}I$ and subjected to immunoprecipitation and SDS-PAGE. The results are shown in FIG. 9 (panel A). Under unreduced conditions, the SN8 immunoprecipitate (FIG. 9A, lane 1) migated on gel electrophoresis as a diffuse single major band at the area of 73–85 kD and another diffused band of higher $M_r$ (probably aggregates), whereas no significant material was present in the immunoprecipitate of an isotype-matched murine control IgG (FIG. 9A, lane 2). Under reduced conditions, the SN8 immunoprecipitate showed three components of approximately 47, 37 and 33 kD (FIG. 9A, lane 3), whereas no bands were evident for the control IgG precipitate (FIG. 9A, lane 4). Thus, the 37 and 33 kD components in FIG. 9A correspond to the major and minor components, respectively, detected in the above Western blotting (FIG. 8B).

The radioimmunoprecipitation and SDS-PAGE were also carried out using a $^{125}$I-labeled antigen preparation from B PLL cells; this antigen preparation was isolated from cell membrane glycoprotein mixtures. In FIG. 9 (panel B), the immunoprecipitated SN8 antigen from the $^{125}$I-labeled B PLL antigen preparation is shown. Under unreduced conditions, the SN8 immunoprecipitate (FIG. 9B, lane 1) showed a single major component of approximately 80 kD, whereas under reduced conditions, I the SN8 immunoprecipitate showed two components of approximately 49 kD and 40 kD (FIG. 9B, lane 3). The control IgG did not precipitate any significant component under either unreduced or reduced conditions (FIG. 9B, lanes 2 and 4). Thus, SN8 immunoprecipitated a disulfide-liked heterodimer, consisting of a 47–49 kD (α chain) and a 37–40 kD (β chain) component, from both BALL-1 and B PLL antigen preparations. In the case of the BALL-1 antigen, SN8 immunoprecipitated an additional minor 33 kD component. This component is probably disulfide-linked to the α chain. This assumption is based on the facts that under unreduced conditions, the 33 kD component was not detected, but a minor component with a slightly lower $M_r$ than 80 kD was detected in both Western blot analysis (FIG. 9A) and radioimmunoprecipitation (FIG. 9A, lane 1) of the BALL-1 antigen preparation. The 33 kD component is apparently an alternative form of the 37–40 kD component since both share the epitope recognized by SN8. Recently, Nakamura et al. ("Heterogeneity of immunoglobulin-associated molecules on human B cells identified by monoclonal antibodies" Proc. Natl. Acad. Sci., USA, 89: 8522, 1992) and Clark et al. ("Human pre-B and B cell membrane μ-chains are noncovalently associated with a disulfide-linked complex containing a product of the B29 gene" J. Immunol. 149: 2857, 1992) detected a similar 33–34 kD component in the lysates of human B and pre-B cells. This 33 kD component is probably the human homologue of the murine Ig-γ which is a variant of Ig-β.

In order to identify the protein detected by SN8, Applicant determined the amino-terminal amino acid sequences of the individual components of the heterodimer. To this end, the SN8 antigen purified from BALL-1 cells by immunoaffinity chromatography was concentrated, reduced, and subjected to SDS-PAGE. The separated proteins in SDS-PAGE were electroblotted to a PVDF transfer membrane (Immobilon-P, Millipore) and the transferred proteins were detected by staining with Coomassie Blue R-250 (FIG. 10). In a parallel experiment, the β chain component on the transfer membrane was detected by Western blot analysis. The 37 kD component detected by Coomassie Blue staining and Western blotting was observed as a diffuse band. In some experiments of SDS-PAGE followed by electroblotting, this protein band appeared to be composed of two closely situated protein bands. Therefore, this diffuse protein band on PVDF membranes was cut into two portions, the upper and lower portions, as indicated in FIG. 10; they were analyzed separately by amino-terminal amino acid sequencing using an amino acid sequencer. An identical amino-terminal sequence was obtained for the first 14 amino acid residues for the two protein samples. In addition, arginine was identified for the 17th position for the lower band material. The sequence is presented in FIG. 11. The amino-terminal sequence for the first 14 amino acid residues of the 37 kD β chain agreed completely to a portion (position 29 to 42) of the deduced amino acid sequence from a recently determined nucleotide sequence of a human B29 cDNA clone; this cDNA clone was selected from a human tonsil cDNA library by screening with a $^{32}$P-labeled probe consisting of a 1153-bp DNA fragment from a full-length murine B29 cDNA clone. The deduced amino acid residues for the positions 15, 16 and 17 were a half cystine, serine and arginine, respectively. Muller et al. compared their deduced amino acid sequence with the amino acid sequence of murine B29 protein and suggested that the human B29 protein possesses a 30-amino acid leader sequence and an extracellular domain of 129 amino acids whose amino-terminal sequence is Amino Acids 3–7 of SEQUENCE ID: NO. 1 ("Cloning and sequencing of the cDNA encoding the human homologue of the murine immunoglobulin-associated protein B29" Eur. J. Immunol., 22: 1621, 1992). However, Applicant's results clearly show that the amino-terminal sequence of the human homologue of the murine B29 protein is Amino Acids 1–7 of SEQUENCE ID: NO. 1 indicating that the human B29 homologue has a 28-amino acid leader sequence and an extracellular domain of 131 amino acids. In FIG. 11, the amino-terminal sequence of the human homologue of the murine B29 protein (hitherto called the human B29 protein) is presented Concerning the α chain component of the heterodimer isolated from BALL-1, two closely situated protein bands were detected by Coomassie staining at the area of the g chain (47 kD) after the reduced BALL-1 antigen preparation was subjected to SDS-PAGE followed by electroblotting to a PVDF membrane. These bands were cut out and analyzed separately by amino acid sequencing. The two samples showed an identical amino-terminal sequence, which was found to correspond to a portion (position 33 to 52) of the deduced amino acid sequence from a recently reported nucleotide sequence of human mb-1 cDNA clones (Yu et al. "Human mb-1 gene: Complete cDNA sequence and its expression in B cells bearing membrane Ig of various isotypes" J. Immunol., 148: 633, 1992; Ha et al. "Molecular cloning and expression pattern of a human gene homologous to the murine mb-1 gene" J. Immunol. 148: 1526, 1992). The identified human mb-1 protein bands are indicated in FIG. 10 and the determined amino-terminal sequence of this protein is presented in FIG. 11.

The determined amino-terminal amino acid sequence of the human mb-1 protein is consistent with the predicted length (32 amino acid residues) of the leader sequence and the predicted amino-terminal amino acid sequence of the human mb-1 gene product.

The above results (FIGS. 10 and 11) demonstrate the molecular heterogeneity of the human mb-1 protein and perhaps also the human B29 protein. Campbell et al. J. Immunl. 147: 1573, 1991 reported a similar difference in the migration on SDS-PAGE between two murine mb-1 proteins, termed pp32 and pp33, each of which was associated with either mIgM or mIgD on murine B cells. They attributed this difference to the differential glycosylation of the proteins. The human B29 and mb-1 proteins that were used for amino acid sequencing in the present study were isolated from BALL-1 cells that expressed both mIgM and mIgD. Therefore, the Applicant's observation of the molecular heterogeneity of the human mb-1 protein appears to be consistent with that of Campbell et al.

Recently, human homologues of the mouse B29 and mb-1 proteins were reported (Nakamura et al. "Heterogeneity of immunoglobulin-associated molecules on human B cells identified by monoclonal antibodies" *Proc. Natl. Acad. Sci., USA*, 89: 8522, 1992; Van Noesel et al. "Identification of two distinct phosphoproteins as components of the human B cell antigen receptor complex" *Eur. J. Immunol.*, 20: 2789, 1990). Most of the data in these reports involved radioimmunoprecipitation followed by SDS-PAGE or Western blot analysis. The putative B29 and mb-1 protein homologues from human B cells were detected as a 37–40 kD and a 47–50 kD component, respectively, under reduced conditions. Under unreduced conditions, they were detected as a heterodimer of a 82–95 kD antigen. In this invention, Applicant detected a heterodimeric antigen composed of a 37–40 kD and a 47–49 kD component in the antigen preparations from two human B leukemia samples by using radioimmunoprecipitation followed by SDS-PAGE and Western blot analysis. In addition, Applicant isolated the non-radiolabeled human homologues and chemically identified them as the human B29 and mb-1 proteins by determining the amino-terminal amino acid sequences of the individual proteins. This appears to be the first unequivocal chemical identification of the human B29 and mb-1 proteins.

As described above, Applicant generated three mAbs, termed SN8, SN8a and SN8b, by an unconventional approach, i.e., immunizing mice with an antigen preparation isolated from B PLL cells rather than immunizing mice with intact cells. The antigen preparation was isolated from the cell membrane glycoproteins using Applicant's previously developed procedure (Seon et al. "Human T cell leukemia antigens on the cell membranes: Purification, molecular characterization, and preparation of specific antisera" *J. Immunol.* 127: 2580, 1981). Analyses of the reactivities of these mAbs with various human leukemia-lymphoma specimens showed that each of them reacted with an extracellular epitope of a cell membrane antigen on human B leukemia-lymphoma cells, particularly with B PLL, B non-Hodgkins' lymphoma and B ALL cells. These monoclonal antibodies also reacted with normal human B cells. However, these mAbs showed no significant reactivity with normal human peripheral blood T cells, granulocytes, monocytes, erythrocytes or platelets. The cell membrane antigen defined by these mAbs was studied using $^{125}$I-labeled antigen preparations isolated from B PLL cell membranes. The antigen was determined to be a disulfide-linked heterodimeric glycoprotein complex with an approximate $M_r$ of 81 kD; the complex was composed of 49 kD (termed α chain) and a 40 kD (β chain) component. Western blot analyses revealed that the epitopes defined by SN8 and SN8a reside on the β chain while SN8b epitope could not be localized to an individual chain.

Use of SN8 was indispensable for the isolation and immunological analysis of the human mb-1 and B29 heterodimer in the present invention. For unknown reasons, it is extremely difficult to generate a mAb defining the human B29 or mb-1 protein by conventional approach, i.e., immunizing mice with human B cells. Thus, few mAbs specific for an extracellular epitope of the human B29 or mb-1 protein have been previously reported. An exception is a recent report by Nakamura et al. ("Heterogeneity of immunoglobulin-associated molecules on human B cells identified by monoclonal antibodies" *Proc. Natl. Acad. Sci., USA*, 89: 8522, 1992) who generated two mAbs defining the putative human equivalent of the mouse B29 protein. Nakamura et al. used an elaborate procedure including repeated injections of mice with proteins separated by SDS-PAGE. Nakamura et al. used the phrase "putative human equivalent of the moust B29 protein" because they had neither characterized the antigen chemically nor determined the antigen's amino acid sequence. Also, it appears that no amino acid sequence of the human B29 or mb-1 proteins has been reported prior to the present invention. SN8, SN8a and SN8b will be very valuable for studying human antigen receptor complex as well as the human B29 and mb-1 heterodimer on normal and malignant human B cells.

Modifications of the present invention will be apparent to those skilled in the art. It is, therefore, intended that the general invention be limited only by the scope of the following claims.

TABLE 1

Reactivity of SN8 Series mAbs with Malignant or EB Virus-Transformed Human Hematopoietic Cell Lines

| Cell Line | Origin of Cell Line | Reactivity (cpm) | | | |
|---|---|---|---|---|---|
| | | SN8 | SN8a | SN8b | Control* |
| HLL pre-B | | | | | |
| NALM-1 | CML-BC† | 444 ± 74 | 371 ± 36 | 351 ± 11 | 447 ± 80 |
| NALM-6 | ALL | 694 ± 325 | 309 ± 18 | 423 ± 63 | 470 ± 145 |
| HLL non-T/non-B | | | | | |
| KM-3 | ALL | 284 ± 33 | 255 ± 31 | 414 ± 28 | 341 ± 75 |
| NALM-16 | ALL | 341 ± 81 | 267 ± 18 | 304 ± 51 | 314 ± 32 |
| REH | ALL | 158 ± 27 | 233 ± 29 | 204 ± 24 | 165 ± 18 |
| HLL B | | | | | |
| BALL-1 | ALL | 5867 ± 519 | 4946 ± 1024 | 4718 ± 252 | 279 ± 31 |
| BALM-2 | ALL | 551 ± 104 | 566 ± 73 | 481 ± 99 | 574 ± 62 |
| Daudi | BL | 3077 ± 366 | 3562 ± 519 | 3250 ± 196 | 344 ± 55 |
| SU-DHL-4 | HL | 8030 ± 1015 | 7223 ± 121 | 6378 ± 229 | 414 ± 69 |
| U689-M | LS | 2703 ± 264 | 2771 ± 485 | 2271 ± 670 | 266 ± 1 |
| Ramos | BL | 4432 ± 1157 | 4032 ± 377 | 2814 ± 352 | 468 ± 16 |
| Raji | BL | 584 ± 127 | 730 ± 85 | 528 ± 9 | 454 ± 93 |
| BALM-3 | LY | 5382 ± 420 | 5330 ± 598 | 4839 ± 199 | 470 ± 65 |
| BALM-5 | LY | 1578 ± 220 | 1831 ± 326 | 1532 ± 115 | 282 ± 49 |
| MO 1043 Plasma | CLL | 227 ± 18 | 255 ± 20 | 244 ± 19 | 269 ± 46 |

TABLE 1-continued

Reactivity of SN8 Series mAbs with Malignant or EB Virus-Transformed Human Hematopoietic Cell Lines

| Cell Line | Origin of Cell Line | Reactivity (cpm) | | | |
|---|---|---|---|---|---|
| | | SN8 | SN8a | SN8b | Control* |
| ARH-77 | MM | 288 ± 48 | 451 ± 70 | 250 ± 42 | 280 ± 17 |
| RPMI 8226 | MM | 232 ± 19 | 415 ± 85 | 217 ± 30 | 242 ± 27 |
| HS | MM | 221 ± 46 | 581 ± 62 | 285 ± 55 | 389 ± 41 |
| HLL T | | | | | |
| MOLT 4 | ALL | 242 ± 136 | 259 ± 74 | 221 ± 69 | 246 ± 57 |
| JM | ALL | 233 ± 60 | 242 ± 27 | 155 ± 28 | 233 ± 37 |
| CCRF-HSB-2 | ALL | 200 ± 14 | 227 ± 47 | 217 ± 33 | 197 ± 14 |
| Ichikawa | ALL | 192 ± 5 | 304 ± 48 | 223 ± 46 | 251 ± 40 |
| HPB-MLT | LTL | 283 ± 54 | 312 ± 56 | 278 ± 34 | 281 ± 26 |
| HUT 78 | SS | 226 ± 23 | 366 ± 57 | 298 ± 87 | 344 ± 85 |
| HLL myelo/monocytic | | | | | |
| ML-2 | AML | 339 ± 28 | 387 ± 63 | 342 ± 15 | 384 ± 69 |
| HL-60 | APL | 166 ± 36 | 219 ± 24 | 601 ± 347 | 217 ± 31 |
| U937 | HL | 346 ± 105 | 300 ± 67 | 246 ± 19 | 230 ± 44 |
| HLL myeloerythroid | | | | | |
| K562 | CML-BC | 223 ± 10 | 261 ± 58 | 219 ± 32 | 205 ± 62 |
| EB virus-transformed B | | | | | |
| CCRF-SB | | 165 ± 14 | 246 ± 50 | 254 ± 50 | 216 ± 36 |
| RPMI 8057 | | 224 ± 94 | 321 ± 53 | 293 ± 62 | 321 ± 103 |

The reactivity was determined using 20 µl of a 10-fold dilution of culture fluids of individual hybridomas and $2 \times 10^5$ cells in each test by means of a cellular RIA. Each test was carried out in triplicate and the values given are the means ± SD.

*An isotype-matching (IgG1) murine plasmacytoma IgG (10 µg/ml) dissolved in the hybridoma culture medium.

†Abbreviations used in this table: CML-BC, chronic myelocytic leukemia in blast crisis; ALL, acute lymphoblastic leukemia; BL, Burkitt's lymphoma; HL, histiocytic lymphoma; LS, lymphosarcoma; LY, lymphoma; CLL, chronic lymphocytic leukemia; MM, multiple myeloma; LTL, leukemic phase of T cell lymphoma; SS, Sezary syndrome; AML, acute myelocytic leukemia, APL, acute promyelocytic leukemia.

What is claimed is:

1. A Monoclonal antibody, from a series designated SN8, which binds to extracellular epitopes of a unique heterodimeric glycoprotein consisting of the human mb-1 protein and the human B29 protien and, which specifically binds to representatives from each of the leukemia lymphoma cell specimens selected from the group consisting of B prolymphocytic leukemia cells, B non-Hodgkin's lymphoma cells, B chronic lymphocytic leukemia cells, B hairy cell leukemia cells, B acute lymphoblastic leukemia cells, and which binds to human normal B cells.

2. A monoclonal antibody of claim 1 designated SN8 produced by hybridoma cell line 3A2-2E7 ATCC deposit number HB11413 and clones thereof.

3. A monoclonal antibody of claim 1 designated SN8a produced by hybridoma cell line 3B3-1D2 ATCC deposit number HB11411 and clones thereof.

4. A monoclonal antibody of claim 1 designated SN8b produced by hybridoma cell line Q6-1D5 ATCC deposit number HB11412 and clones thereof.

5. Fragments of monoclonal antibody SN8 of claim 2 wherein the fragments comprise F(ab')$_2$, Fab', Fab, Fv, Fd' or Fd.

6. Fragments of monoclonal antibody SN8a of claim 3 wherein the fragments comprise F(ab')$_2$, Fab', Fab, Fv, Fd' or Fd.

7. Fragments of monoclonal antibody SN8b of claim 4 wherein the fragments comprise (F(ab')$_2$, Fab', Fab, Fv, Fd' or Fd.

8. A hybridoma cell line designated ATCC HB11413 for producing the monoclonal antibody of claim 2.

9. A hybridoma cell line designated ATCC HB11413 for producing the monoclonal antibody of claim 3.

10. A hybridoma cell line designated ATCC HB11412 for producing the monoclonal antibody of claim 4.

11. A diagnostic kit comprising the monoclonal antibodies of claim 1 within a package.

12. A method for producing the monoclonal antibodies of claim 1 comprising the steps of:

(a) preparing cell membranes from B prolymphocytic leukemia cells and cell membrane antigens by solubilizing by deoxycholate treatment to obtain solubilized antigens;

(b) fractionating the solubilized antigens by affinity chromatography on serially connected columns of *Lens culinaris* lectin (LcH) and *Ricinis communis* lectin (RCA);

(c) individually eluting the LcH-bound and RCA-bound glycoconjugates which result from step (b);

(d) combining the individually eluted glycoconjugates of step (c);

(e) submitting the combined glycoconjugates of step (d) to passive immunoaffinity chromatography;

(f) pooling and concentrating materials in passthrough fractions obtained from step (e) to obtain an isolated antigen preparation;

(g) immunizing mice or rats with the isolated antigen preparation obtained from step (f);

(h) obtaining immune spleen cells from said mice or rats after step (g) and fusing the immune spleen cells with an appropriate myeloma cell line to obtain hybridomas; and (i) screening antibodies from the hybridomas to obtain desired hybridomas which produce an SN8 series antibody and cloning the desired hybridomas.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 17 amino acid residues
        ( B ) TYPE: amino acid
        ( C ) STRANDEDNESS: Not Relevant
        ( D ) TOPOLOGY: Not Relevant ( i i ) MOLECULE TYPE: Protein ( i i i ) HYPOTHETICAL: No ( i v ) ANTI-SENSE: No ( v ) FRAGMENT TYPE: N-terminal fragment ( v i ) ORIGINAL SOURCE:
        ( A ) ORGANISM: Human lymphoid cells
        ( B ) STRAIN: N/A
        ( C ) INDIVIDUAL ISOLATE: N/A
        ( D ) DEVELOPMENTAL STAGE: N/A
        ( E ) HAPLOTYPE: N/A
        ( F ) TISSUE TYPE: N/A
        ( G ) CELL TYPE: N/A
        ( H ) CELL LINE: BALL-1
        ( I ) ORGANELLE: N/A (v i i) IMMEDIATE SOURCE: N/A
    (A) LIBRARY:
    (B) CLONE:

(v i i i) POSITION IN GENOME: N/A
    (A) CHROMOSOME/SEGMENT:
    (B) MAP POSITION:
    (C) UNITS:

(i x) FEATURE:
    (A) NAME/KEY: Human B-29 protein amino-terminal amino acid sequence
    (B) LOCATION: N/A
    (C) IDENTIFICATION METHOD: N- terminal amino acid sequence determination by use of a protein sequencer
    (D) OTHER INFORMATION: N/A (x) PUBLICATION INFORMATION: N/A
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(x i) SEQUENCE DESCRIPTION: SEQ ID NO: 1:

```
Ala  Arg  Ser  Glu  Asp  Arg  Tyr  Arg  Asn  Pro  Lys  Gly  Ser  Ala  Xaa  Xaa  Arg   (17)
 1              5                        10                       15
```

(2) INFORMATION FOR SEQ ID NO: 2:

(i) SEQUENCE CHARACTERISTICS:
        (A) LENGTH: 20 amino acid residues
        (B) TYPE: amino acid
        (C) STRANDEDNESS: Not Relevant
        (D) TOPOLOGY: Not Relevant (i i) MOLECULE TYPE: Protein (i i i) HYPOTHETICAL: No (i v) ANTI-SENSE: No (v) FRAGMENT TYPE: N-terminal fragment (v i) ORIGINAL SOURCE:
        (A) ORGANISM: Human lymphoid cells
        (B) STRAIN: N/A
        (C) INDIVIDUAL ISOLATE: N/A
        (D) DEVELOPMENTAL STAGE: N/A
        (E) HAPLOTYPE: N/A
        (F) TISSUE TYPE: N/A
        (G) CELL TYPE: N/A
        (H) CELL LINE: BALL-1
        (I) ORGANELLE: N/A (v i i) IMMEDIATE SOURCE: N/A
        (A) LIBRARY:
        (B) CLONE:

(v i i i) POSITION IN GENOME: N/A
        (A) CHROMOSOME/SEGMENT:
        (B) MAP POSITION:
        (C) UNITS:

(i x) FEATURE:
        (A) NAME/KEY: Human MB-1 protein amino-terminal amino acid sequence
        (B) LOCATION: N/A
        (C) IDENTIFICATION METHOD: N- terminal amino acid sequence determination by use of a protein sequencer
        (D) OTHER INFORMATION: N/A

```
( x ) PUBLICATION INFORMATION: N/A
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO: 2:

Leu  Trp  Met  His  Lys  Val  Pro  Ala  Ser  Leu  Met  Val  Ser  Leu  Gly              (20)
 1              5                        10                       15

Glu  Asp  Ala  His  Phe
                20
```